US008460177B2

(12) United States Patent
Kawano et al.

(10) Patent No.: US 8,460,177 B2
(45) Date of Patent: Jun. 11, 2013

(54) CAPSULE MEDICAL DEVICE GUIDANCE SYSTEM AND METHOD FOR GUIDING CAPSULE MEDICAL DEVICE

(75) Inventors: Hironao Kawano, Machida (JP);
Henrik Keller, Erlangen (DE);
Aleksandar Juloski, Nuremberg (DE)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/214,510

(22) Filed: Aug. 22, 2011

(65) Prior Publication Data
US 2012/0095289 A1  Apr. 19, 2012

Related U.S. Application Data

(63) Continuation of application No. PCT/JP2010/064109, filed on Aug. 20, 2010.

(30) Foreign Application Priority Data

Nov. 10, 2009  (JP) ................. 2009-257346

(51) Int. Cl.
*A61B 1/00* (2006.01)
*A61B 1/04* (2006.01)
(52) U.S. Cl.
CPC ............. *A61B 1/00158* (2013.01); *A61B 1/041* (2013.01)
USPC ............................ 600/114; 600/117; 600/118
(58) Field of Classification Search
USPC ................... 600/114, 117, 118, 424; 335/219
See application file for complete search history.

(56) References Cited

U.S. PATENT DOCUMENTS

| 6,939,292 | B2 | 9/2005 | Mizuno | |
|---|---|---|---|---|
| 7,182,089 | B2* | 2/2007 | Ries | 128/899 |
| 8,235,888 | B2* | 8/2012 | Kawano | 600/118 |

(Continued)

FOREIGN PATENT DOCUMENTS

| JP | 2005-193066 A | 7/2005 |
|---|---|---|
| JP | 2005-277740 A | 10/2005 |

(Continued)

OTHER PUBLICATIONS

International Search Report dated Sep. 21, 2010 in related Japanese Patent Application No. PCT/JP2010/064109.

(Continued)

*Primary Examiner* — John P Leubecker
(74) *Attorney, Agent, or Firm* — Scully, Scott, Murphy & Presser, PC.

(57) ABSTRACT

A system and method for guiding a capsule medical device. The method includes: changing, by a control unit, a gradient distribution of a gradient magnetic field generated by a magnetic field generator in a vertical direction, the magnetic field generator generating at least the gradient magnetic field in the vertical direction to guide a capsule medical device that includes a magnetic-field responding unit; detecting, by a position detector, a position of the capsule medical device in the vertical direction based on a gradient distribution of the gradient magnetic field generated by the magnetic field generator, a physical parameter of the capsule medical device, and a physical parameter of a liquid when the capsule medical device starts to move; and setting, by the control unit, the magnetic field generated by the magnetic field generator based on the detected position of the capsule medical device in the vertical direction.

14 Claims, 18 Drawing Sheets

U.S. PATENT DOCUMENTS

| | | | |
|---|---|---|---|
| 8,241,206 B2 * | 8/2012 | Kawano | 600/117 |
| 8,303,485 B2 * | 11/2012 | Segawa et al. | 600/117 |
| 8,308,632 B2 * | 11/2012 | Bechtold et al. | 600/117 |
| 2005/0085696 A1 * | 4/2005 | Uchiyama et al. | 600/160 |
| 2007/0221233 A1 | 9/2007 | Kawano et al. | |
| 2008/0306340 A1 * | 12/2008 | Uchiyama et al. | 600/117 |
| 2009/0093678 A1 * | 4/2009 | Kimura et al. | 600/117 |
| 2009/0227864 A1 | 9/2009 | Sato et al. | |
| 2010/0010304 A1 | 1/2010 | Kawano | |
| 2010/0049033 A1 * | 2/2010 | Kawano et al. | 600/424 |
| 2010/0168516 A1 | 7/2010 | Uchiyama | |
| 2010/0268026 A1 * | 10/2010 | Takizawa | 600/109 |
| 2011/0009697 A1 * | 1/2011 | Kawano et al. | 600/117 |
| 2012/0203068 A1 * | 8/2012 | Sato et al. | 600/117 |

FOREIGN PATENT DOCUMENTS

| | | |
|---|---|---|
| JP | 2006-058501 A | 3/2006 |
| JP | 2009-213613 A | 9/2009 |
| JP | 2010-017554 A | 1/2010 |
| WO | WO 2007/077922 A1 | 7/2007 |
| WO | WO 2009/34844 A1 | 3/2009 |

OTHER PUBLICATIONS

Decision of a Patent Grant dated Nov. 8, 2011 in corresponding Japanese Patent Application No. 2011-532391 together with partial English translation.

* cited by examiner

CAPSULE MEDICAL DEVICE GUIDANCE SYSTEM AND METHOD FOR GUIDING CAPSULE MEDICAL DEVICE

CROSS-REFERENCE TO RELATED APPLICATION

This application is a continuation of PCT international application Ser. No. PCT/JP2010/064109 filed on Aug. 20, 2010 which designates the United States, incorporated herein by reference, and which claims the benefit of priority of Japanese Patent Application No. 2009-257346, filed on Nov. 10, 2009, incorporated herein by reference.

BACKGROUND OF THE INVENTION

1. Field of the Invention

The present invention relates to a capsule medical device guidance system and a method for guiding a capsule medical device in which a capsule medical device to be inserted inside a subject is guided.

2. Description of the Related Art

Conventionally, a capsule medical device provided with an imaging function and a radio communication function within a casing of a capsule shape formed in a size allowing insertion into an inside of a digestive canal of a subject such as a patient has appeared in the field of an endoscope. The capsule medical device, after being swallowed from a mouth of the subject, travels inside the digestive canal according to its peristalsis and the like. The capsule medical device sequentially obtains images inside organs of the subject (hereinafter sometimes referred to as "in-vivo images") and sequentially transmits the obtained in-vivo images wirelessly to a receiver placed outside the subject until it is naturally excreted after inserted inside the digestive canal of the subject.

The in-vivo images captured by the capsule medical device are imported into an image displaying device via the receiver. The image displaying device displays the imported in-vivo images statically or dynamically. A user such as a doctor or a nurse observes the in-vivo images of the subject displayed on the image displaying device to examine the inside of organs of the subject through the observation.

Besides, a capsule medical device guidance system in which the capsule medical device inside the subject is guided by a magnetic force (hereinafter referred to as a "magnetic guidance") has been proposed in recent years. In the capsule medical device guidance system, the capsule medical device is generally further provided with a permanent magnet inside the capsule-shaped casing and the image displaying device displays the in-vivo images sequentially captured by the capsule medical device inside the subject in real time. In the capsule medical device guidance system, a magnetic field is applied to the capsule medical device inside the subject and the capsule medical device inside the subject is magnetically guided to a desired position by the magnetic force generated by the applied magnetic field. The user uses an operation unit of the capsule medical device guidance system to operate the magnetic guidance of the capsule medical device while referring to the in-vivo images displayed on the image displaying device.

As the capsule medical device, a capsule endoscope which, for observing the inside of organs such as a stomach or a large intestine having a comparatively large space, has a specific gravity enabling floating on a liquid injected inside such organs and sequentially captures in-vivo images in a floating state on the liquid is available. To examine the inside of the organs such as a stomach having a comparatively large space intensively, there is a case in which a liquid which makes the inside of the organ (a fold of an inner wall of the organ, specifically) stretch and the capsule endoscope having a lower specific gravity than the liquid are ingested (see International Publication No. 2007/077922, for example). In this case, the capsule endoscope sequentially captures images inside the organ which has stretched due to the liquid while floating on a surface of the liquid in a manner of taking a predetermined attitude (a vertical attitude in which a central axis in a longitudinal direction of the capsule endoscope becomes perpendicular to the surface of the liquid, for example) in the inside of the organ such as a stomach. The capsule endoscope is capable of capturing images inside the organ over a wide range by travelling in a desired direction in the state of floating on the surface of the liquid inside the organ.

SUMMARY OF THE INVENTION

According to an aspect of the present invention, a capsule medical device guidance system includes a capsule medical device that includes a magnetic-field responding unit; a magnetic field generator that generates at least a gradient magnetic field in a vertical direction for the magnetic-field responding unit to guide the capsule medical device, the magnetic field generator being capable of changing a gradient distribution of the gradient magnetic field to be generated in the vertical direction; an operation input unit through which operating information for magnetically guiding the capsule medical device is input; a control unit that controls the magnetic field generator according to the operating information input through the operation input unit to guide the capsule medical device, the control unit controlling the magnetic field generator to change a gradient distribution of the gradient magnetic field to be generated in the vertical direction; and a position detector that detects a position of the capsule medical device in the vertical direction based on a gradient distribution of the gradient magnetic field generated by the magnetic field generator, a physical parameter of the capsule medical device, and a physical parameter of a liquid when the capsule medical device starts to move, wherein the control unit sets a magnetic field to be generated by the magnetic field generator based on the position of the capsule magnetic device in the vertical direction detected by the position detector.

According to another aspect of the present invention, a method for guiding a capsule medical device includes changing, by a control unit, a gradient distribution of a gradient magnetic field generated by a magnetic field generator in a vertical direction, the magnetic field generator generating at least the gradient magnetic field in the vertical direction to guide a capsule medical device that includes a magnetic-field responding unit; detecting, by a position detector, a position of the capsule medical device in the vertical direction based on a gradient distribution of the gradient magnetic field generated by the magnetic field generator, a physical parameter of the capsule medical device, and a physical parameter of a liquid when the capsule medical device starts to move; and setting, by the control unit, the magnetic field generated by the magnetic field generator based on the detected position of the capsule medical device in the vertical direction.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 18B is a right side view of the operation input unit shown in FIG. 18A;

DETAILED DESCRIPTION OF THE PREFERRED EMBODIMENTS

Exemplary embodiments of a capsule medical device guidance system according to the present invention will be explained below by taking, as an example, a capsule medical device guidance system in which a capsule endoscope which is inserted inside a subject via a mouth and floats on a liquid stored in a stomach, a small intestine, a large intestine, and the like of the subject is used as a body-insertable device. However, the present invention is not limited to this configuration and any body-insertable devices of various kinds including, for example, a monocular or pantoscopic capsule endoscope that executes an imaging operation on the way travelling from an esophagus to an anus of a subject in a lumen to obtain in-vivo images inside the subject can be used. It should be noted that the present invention is not limited to the embodiments. The same part is assigned with the same reference symbol in the description of the drawings.

First Embodiment

Figure 1:
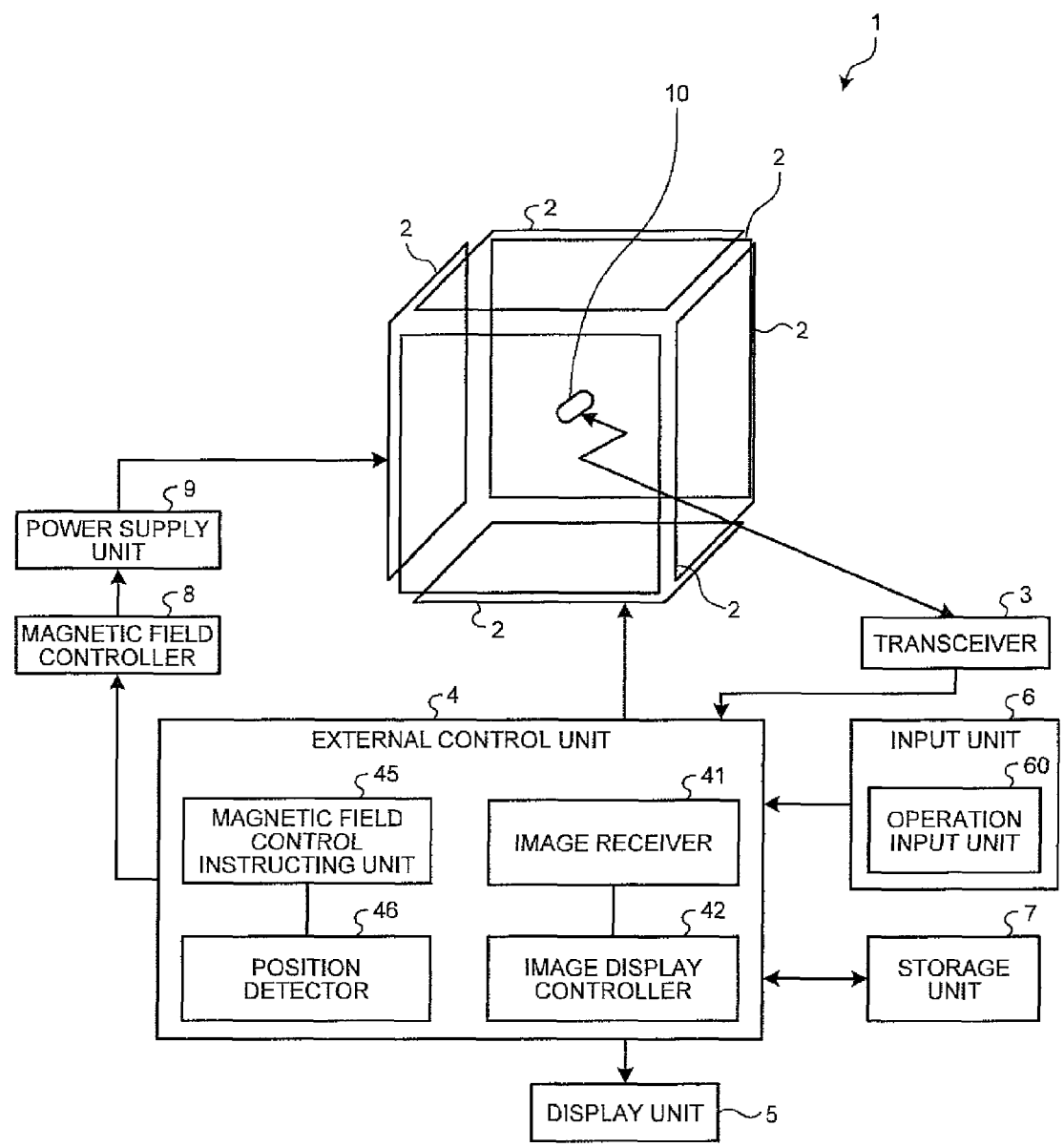
FIG. 1 is a view of an entire structure of a capsule medical device guidance system according to a first embodiment.

A first embodiment will be explained first. FIG. 1 is a view of an entire structure of a capsule medical device guidance system according to a first embodiment of the present invention. As shown in FIG. 1, a capsule medical device guidance system 1 according to the first embodiment is provided with a capsule endoscope 10 as a capsule medical device that is inserted, by being swallowed from a mouth of a subject, to an inside of a body cavity inside the subject and performs a communication with an external device; a magnetic field generator 2 that is provided around the subject and capable of generating a three-dimensional magnetic field; a transceiver 3 that performs a radio communication with the capsule endoscope 10 to receive a radio signal containing an image captured by the capsule endoscope 10 as well as to transmit an operation signal to the capsule endoscope 10; an external control unit 4 that controls each component of the capsule medical device guidance system 1; a display unit 5 that outputs and displays the images captured by the capsule endoscope 10; an input unit 6 through which instructing information for instructing various operations such as operating information for magnetically guiding the capsule endoscope 10 in the capsule medical device guidance system 1 is input to the external control unit 4; a storage unit that stores image information captured by the capsule endoscope 10 and the like; a magnetic field controller 8 that controls a magnetic field involved in the magnetic field generator 2; and a power supply unit 9 that supplies a power to the magnetic field generator 2 depending on the control by the magnetic field controller 8. The capsule endoscope 10 is a capsule medical device that obtains in-vivo images of the subject and incorporates an imaging function and a radio communication function. The capsule endoscope 10 is inserted inside organs of the subject through an oral ingestion and the like. After the insertion, the capsule endoscope 10 inside the subject travels inside the digestive canal and is eventually excreted to the outside of the subject. The capsule endoscope 10 sequentially captures in-vivo images of the subject during the period after inserted to the inside until excreted to the outside of the subject, and wirelessly transmits the obtained in-vivo images sequentially to the transceiver 3 placed outside the subject. Besides, the capsule endoscope 10 includes therein a magnetic body such as a permanent magnet. The capsule endoscope 10 floats on a liquid injected inside organs (inside a stomach, for example) of the subject and is magnetically guided by the magnetic field generator 2 placed outside the subject.

The magnetic field generator 2 serves to magnetically guide the capsule endoscope 10 inside the subject. The magnetic field generator 2 is, for example, realized by using a coil and the like and generates a guiding magnetic field by using a power supplied by the power supply unit 9. The magnetic field generator 2 applies the generated guiding magnetic field to the magnetic body inside the capsule endoscope 10 and magnetically captures the capsule endoscope 10 due to the action of the guiding magnetic field. The magnetic field generator 2 controls a three-dimensional attitude of the capsule endoscope 10 inside the subject by changing a direction of the guiding magnetic field acting on the capsule endoscope 10 inside the subject. The magnetic field generator 2 is capable of generating, in addition to a so-called uniform magnetic field, a gradient magnetic field in which a magnetic field intensity verges sparsely to densely and a peak magnetic field which has a peak at a given position on a horizontal surface and captures the capsule endoscope 10 in the vicinity of the position where the peak arises. The magnetic field generator 2 is capable of generating a gradient magnetic field in a vertical direction and also changing a gradient distribution of the gradient magnetic field in the vertical direction.

The transceiver 3 is provided with a plurality of antennas and receives in-vivo images of the subject from the capsule endoscope 10 via the plurality of antennas. The transceiver 3 sequentially receives a radio signal from the capsule endoscope 10 via the plurality of antennas. The transceiver 3 selects an antenna whose receiving electric field intensity is the highest of the plurality of antennas and performs a demodulating process and the like with respect to the radio signal received via the selected antenna from the capsule endoscope 10. Thus, the transceiver 3 extracts image data obtained by the capsule endoscope 10, i.e., in-vivo image data of the subject from the radio signal. The transceiver 3 transmits an image signal containing the extracted in-vivo image data to the external control unit 4.

The external control unit 4 controls operations of the magnetic field generator 2, the display unit 5, the storage unit 7, and the magnetic field controller 8 and controls input and output of signals among these components. The external control unit 4 is provided with an image receiver 41 that sequentially obtains in-vivo images the transceiver 3 had sequentially received and an image display controller 42 that controls the display unit 5 to display in real time in-vivo images the transceiver 3 had sequentially received. Besides, the external control unit 4 controls the storage unit 7 to store a group of in-vivo images of the subject obtained from the transceiver 3.

The external control unit 4 is provided with a magnetic field control instructing unit 45 that instructs, for guiding the capsule endoscope 10 depending on operating information input through the input unit 6, the magnetic field controller 8 about a condition in which a magnetic field is generated and a position detector 46 that detects a position of the capsule endoscope 10 in the vertical direction. The magnetic field control instructing unit 45 instructs the magnetic field controller 8 when the operating information of the capsule endoscope 10 is input through the input unit 6 to generate a magnetic field depending on a direction and a position of the magnetic guidance specified by the input operating information.

The display unit 5 is realized by using display devices of various kinds such as a liquid crystal display device and displays information of various kinds instructed to display by the external control unit 4. Specifically, the display unit 5 displays, for example, the group of in-vivo images of the subject captured by the capsule endoscope 10 based on the control of the image display controller 42 in the external control unit 4. The display unit 5 displays a reduced-size image of the in-vivo image which is selected or marked through an inputting operation by the input unit 6 among the group of the in-vivo images and information of the patient, examination, and the like of the subject.

The input unit 6 is realized by using input devices such as a keyset and a mouse and allows inputting information of various kinds to the external control unit 4 depending on an input operation by an operator such as a doctor. The information of various kinds input through the input unit 6 to the external control unit 4 includes, for example, instructing information for instructing the external control unit 4, patient information and examination information of the subject, and the like. The patient information of the subject specifies the subject, including patient name, patient ID, date of birth, sex, age, and the like of the subject, for example. The examination information of the subject specifies an examination in which the capsule endoscope 10 is inserted inside the digestive canal of the subject to observe therein, including examination ID, date of examination, and the like, for example. The input unit 6 allows inputting operating information for operating the magnetic guidance of the capsule endoscope 10 by the magnetic field generator 2 described above.

The input unit 6 is provided with an operation input unit 60 that allows inputting operating information for magnetically guiding the capsule endoscope 10 such as the magnetic guidance direction, the magnetic guidance position, and the like of the capsule endoscope 10 which is an operation target in the magnetic guidance. The operation input unit 60 has a configuration provided with a joystick, buttons of various kinds, and switches of various kinds and allows inputting operating information to the external control unit 4 through an operation of the joystick and the like by the operator.

The storage unit 7 is realized by using a storage medium such as a flash memory or a hard disk which stores information in a rewritable manner. The storage unit 7 stores various information which the external control unit 4 instructs to store and passes the external control unit 4 information which the external control unit 4 instructs to read out among the stored various information. The various information stored by the storage unit 7 includes, for example, each piece of image data of the group of in-vivo images of the subject captured by the capsule endoscope 10, data of an in-vivo image selected through the input operation of the input unit 6 from the in-vivo images displayed on the display unit 5, information such as patient information of the subject input through the input unit 6, and the like.

The magnetic field controller 8 controls a power distribution amount supplied by the power supply unit 9 to the magnetic field generator 2 based on the instructing information instructed by the external control unit 4 and controls, through the control of this power supply unit 9, the magnetic field generator 2 to generate a guiding magnetic field necessary for the magnetic guidance of the capsule endoscope 10 depending on the magnetic guidance direction and the magnetic guidance position based on the operating information.

The power supply unit 9 supplies a power (alternating current, for example) necessary for generating the guiding magnetic field described above to the magnetic field generator 2 based on the controls of the external control unit 4 and the magnetic field controller 8. In this case, the power supply unit 9 arbitrarily supplies a necessary power to each of a plurality of coils included in the magnetic field generator 2. The direction and the intensity of the guiding magnetic field generated by the magnetic field generator 2 described above are controlled by a power distribution amount from the power supply unit 9 to each coil in the magnetic field generator 2.

Figure 2:
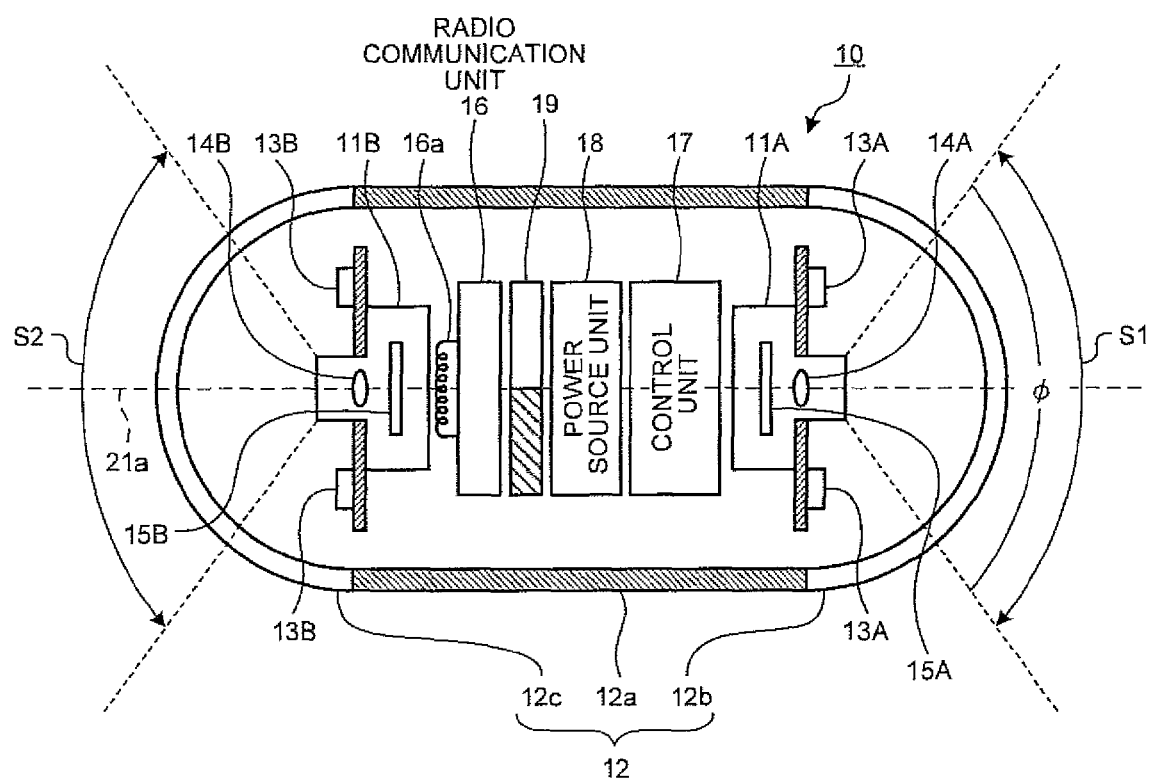
FIG. 2 is a cross-sectional view of an example of a structure of the capsule endoscope shown in FIG. 1.

Next, the capsule endoscope 10 will be explained. FIG. 2 is a cross-sectional view of an example of a structure of the capsule endoscope shown in FIG. 1. As shown in FIG. 2, the capsule endoscope 10 is provided with a capsule-shaped casing 12 which is an exterior formed in a size allowing an easy insertion into the inside of organs of the subject and imaging units 11A and 11B that capture images of the subject in respective imaging directions different to each other. The capsule endoscope 10 is also provided with a radio communication unit 16 that wirelessly transmits each of the images captured by the imaging unit 11A and 11B to the outside, a control unit 17 that controls each component of the capsule endoscope 10, and a power source unit 18 that supplies power to each component of the capsule endoscope 10. The capsule endoscope 10 is further provided with a permanent magnet 19 that enables the magnetic guidance by the magnetic field generator 2 described above.

The capsule-shaped casing 12 is an outer casing formed in a size allowing insertion to the inside of organs of the subject and realized by blocking open ends at both sides of a cylindrical casing 12a with dome-shaped casings 12b and 12c. The dome-shaped casings 12b and 12c are optical members which each have a dome shape and a transparency with respect to a light of a predetermined wavelength band such as a visible light. The cylindrical casing 12a is a colored casing which is nearly opaque with respect to the visible light. The capsule-shaped casing 12 formed by the cylindrical casing 12a and the dome-shaped casings 12b and 12c includes therein the imaging units 11A and 11B, the radio communication unit 16, the control unit 17, the power source unit 18, and the permanent magnet 19 in a liquid-tight manner.

The imaging units 11A and 11B capture images in respective imaging directions different to each other. Specifically, the imaging unit 11A includes an illumination unit 13A such as an LED, an optical system 14A such as a condenser lens, and an imaging element 15A such as a CMOS image sensor or a CCD. The illumination unit 13A emits an illumination light such as a white color light to an imaging field S1 of the imaging element 15A to illuminate the subject within the imaging field S1 (inner wall of organs at a side of the imaging field S1 inside the subject, for example) through the dome-shaped casing 12b. The optical system 14A condenses a reflection light from the imaging field S1 on an imaging surface of the imaging element 15A to form a subject image in the imaging field S1 on the imaging surface of the imaging element 15A. The imaging element 15A receives the reflection light from the imaging field S1 via the imaging surface and performs a photoelectric conversion process with respect to the received optical signal to capture the subject image in the imaging filed S1, i.e., the in-vivo image of the subject. The imaging unit 11B includes an illumination unit 13B such as an LED, an optical system 14B such as a condenser lens, and an imaging element 15B such as a CMOS image sensor or a CCD. The illumination unit 13B emits an illumination light such as a white color light to an imaging field S2 of the imaging element 15B to illuminate the subject within the imaging field S2 (inner wall of organs at a side of the imaging field S2 inside the subject, for example) through the dome-shaped casing 12c. The optical system 14B condenses a reflection light from the imaging field S2 on an imaging surface of the imaging element 15B to form a subject image in the imaging field S2 on the imaging surface of the imaging element 15B. The imaging element 15B receives the reflection light from the imaging field S2 via the imaging surface and performs a photoelectric conversion process with respect to the received optical signal to capture the subject image in the imaging filed S2, i.e., the in-vivo image of the subject.

When the capsule endoscope 10 is a binocular-type capsule endoscope that captures respective images of the front and the rear in a direction of a long axis 21a as shown in FIG. 2, the optical axes of the imaging units 11A and 11B are nearly parallel with or nearly accord with the long axis 21a as a central axis in the longitudinal direction of the capsule casing 12. In addition, the directions of the imaging fields S1 and S2 of the imaging units 11A and 11B, i.e., the imaging directions of the imaging units 11A and 11B are opposite with each other.

The radio communication unit 16 is provided with an antenna 16a and wirelessly transmits the images captured by the imaging units 11A and 11B described above sequentially to the outside via the antenna 16a. Specifically, the radio communication unit 16 obtains from the control unit 17 a signal of an in-vivo image of the subject captured by the imaging units 11A or 11B and performs a demodulation process and the like with respect to the obtained image signal to generate a radio signal obtained via the demodulation of the image signal. The radio communication unit 16 transmits the radio signal to the transceiver 3 placed outside via the antenna 16a.

The control unit 17 controls operations of the imaging units 11A and 11B and the radio communication unit 16 which are components of the capsule endoscope 10 and controls input and output of a signal among these components. Specifically, the control unit 17 controls the imaging element 15A to capture images of the subject in the imaging field S1 illuminated by the illumination unit 13A and the imaging element 15B to capture images of the subject in the imaging field S2 illuminated by the illumination unit 13B. Besides, the control unit 17 includes a signal processing function of generating an image signal. The control unit 17 obtains in-vivo image data in the imaging field S1 from the imaging element 15A and performs a predetermined signal process with respect to the in-vivo image data each time of the obtainment to generate an image signal containing the in-vivo image data in the imaging field S1. Similarly to this, the control unit 17 obtains in-vivo image data in the imaging field S2 from the imaging element 15B and performs a predetermined signal process with respect to the in-vivo image data each time of the obtainment to generate an image signal containing the in-vivo image data in the imaging field S2. The control unit 17 controls the radio communication unit 16 to wirelessly transmit each image signal sequentially to the outside along time series.

The power source unit 18 is a power storage unit such as a button battery or a capacitor and realized by a switch unit such as a magnetic switch. A power source of the power source unit 18 is switched on and off depending on a magnetic field applied from the outside and the power in the power storage unit is arbitrarily supplied to the components (the imaging units 11A and 11B, the radio communication unit 16, and the control unit 17) of the capsule endoscope 10 in the state where the switch is on. In the state where the switch is off, the power source unit 18 stops supplying power to the components of the capsule endoscope 10.

The permanent magnet 19 serves to enable the magnetic guidance of the capsule endoscope 10 by the magnetic field generator 2 described above. The permanent magnet 19 is fixedly arranged inside the capsule-shaped casing 12 in a state of being relatively fixed with respect to the imaging units 11A and 11B described above. In this case, the permanent magnet 19 performs a magnetization in a known direction which is relatively fixed with respect to the vertical direction of respective imaging surfaces of the imaging element 15A and 15B.

Figure 3:
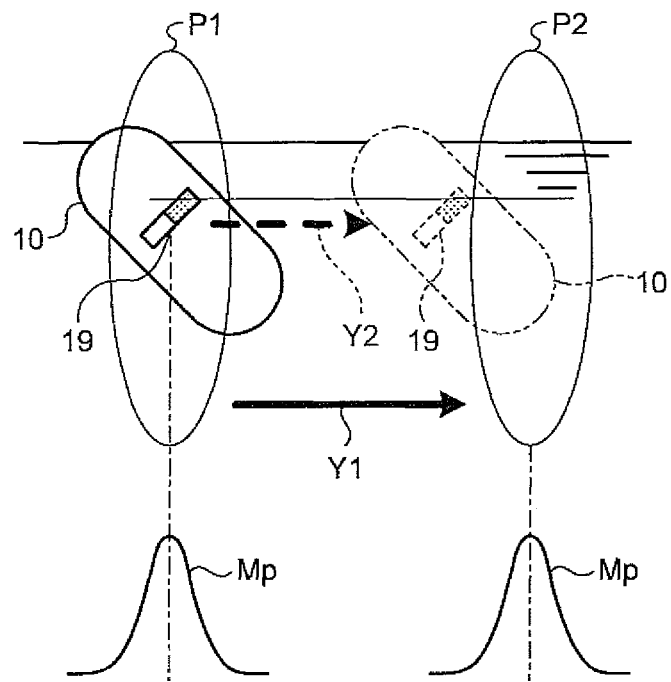
FIG. 3 is an explanatory view of a peak magnetic field generated by the magnetic field generator shown in FIG. 1.
Figure 4:
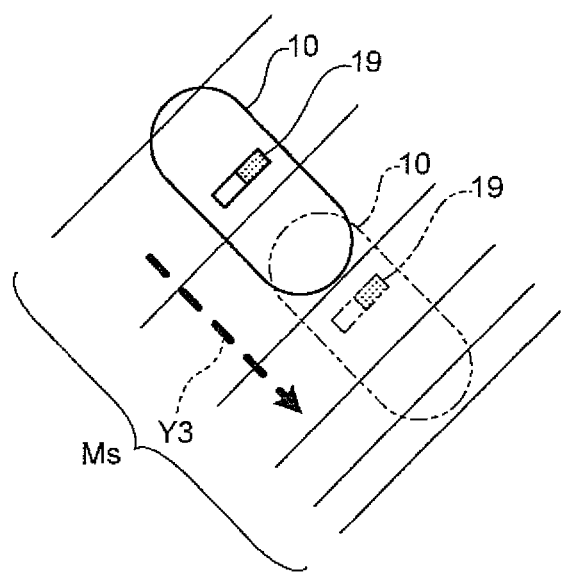
FIG. 4 is an explanatory view of a gradient magnetic field generated by the magnetic field generator shown in FIG. 1.

Next, a kind of the magnetic field to be generated by the magnetic field generator 2 will be explained. The magnetic field generator 2 is capable of generating a peak magnetic field and a gradient magnetic field in addition to a so-called uniform magnetic field. The peak magnetic field has a peak in intensity of the magnetic field in a direction perpendicular to the horizontal surface as shown by a peak magnetic field Mp in FIG. 3. The peak magnetic field Mp is able to attract and capture the permanent magnet 19 to the peak position in the magnetic field intensity. In other words, the peak magnetic field Mp attracts the permanent magnet 19 of the capsule endoscope 10 to a given position in the horizontal direction to capture the capsule endoscope 10. The magnetic field generator 2 is capable of shifting the capsule endoscope 10 from a position P1 to a position P2 as shown by an arrow Y2 by shifting the peak position of the peak magnetic field Mp from the position P1 to the position P2 as shown by an arrow Y1, for example. The gradient magnetic field has a magnetic gradient in which a distribution of magnetic force lines each having a predetermined magnetic field intensity verges sparsely to densely as shown by a gradient magnetic field Ms in FIG. 4. The gradient magnetic field biases the permanent magnet 19 to a direction of verging from a sparse to a dense intensity in the distribution of the magnetic field intensity. The magnetic field generator 2 generates the gradient magnetic field Ms in which the distribution of the magnetic force lines verges sparsely to densely from the upper left direction to the lower right direction, i.e., the gradient magnetic field Ms whose gradient verges from the upper left direction to the lower right direction, for example. The gradient magnetic field Ms provides a magnetic attraction which enables moving from the upper left direction to the lower right direction to the permanent magnet 19 of the capsule endoscope 10, so that the permanent magnet 19 is biased to a direction shown by an arrow Y3. Thus, the gradient magnetic field Ms enables the capsule endoscope 10 to move to a direction shown by the arrow Y3.

For example in a case of pressing the capsule endoscope 10 floating on the liquid against a bottom part of the stomach, it is necessary to generate a gradient magnetic field having a downward gradient for generating a downward magnetic attraction. If the magnetic attraction according to the downward gradient magnetic field is not larger than a resultant force (running in an upper direction in this case) of buoyancy and gravity of the capsule endoscope 10, it is impossible to press the capsule endoscope 10 floating on the liquid against the bottom part of the stomach. Therefore, a gradient magnetic field having a gradient corresponding to a magnetic attraction which becomes larger than the resultant force of the buoyancy and the gravity of the capsule endoscope 10 is able to cause the capsule endoscope 10 to be pressed against the bottom part of the stomach. If the downward magnetic attraction according to the gradient of the gradient magnetic field becomes smaller than the resultant force of the buoyancy and the gravity of the capsule endoscope 10, the capsule endoscope 10 starts to float.

As described, a tilt of the gradient magnetic field corresponding to the magnetic attraction enabling the capsule endoscope 10 to move is determined depending on the buoyancy and the gravity of the capsule endoscope 10. The buoyancy and the gravity of the capsule endoscope 10 are determined based on a physical parameter of the capsule endoscope 10 such as a mass, a volume, and a magnetic moment of the capsule endoscope 10 and on a physical parameter of the liquid such as a density of the liquid on which the capsule endoscope 10 floats. Therefore, the tilt of the gradient magnetic field enabling the capsule endoscope 10 to move is determined based on the mass, the volume, and the magnetic moment of the capsule endoscope 10 and on the density of the liquid on which the capsule endoscope 10 floats.

In the first embodiment, the tilt enabling the capsule endoscope 10 to move is obtained in advance, the magnetic field generator 2 is made to generate a gradient magnetic field whose tilt position enabling the capsule endoscope 10 to operate in the vertical direction to operate is changed, and a position of the capsule endoscope 10 in the vertical direction is obtained based on the gradient distribution of the gradient magnetic field in which the capsule endoscope 10 starts to move.

Figure 5:
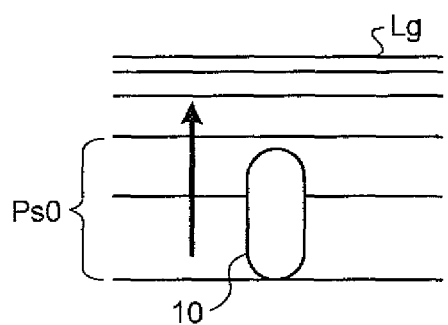
FIG. 5 is an explanatory view of a tilt enabling the capsule endoscope shown in FIG. 1 to start to move.
Figure 6:
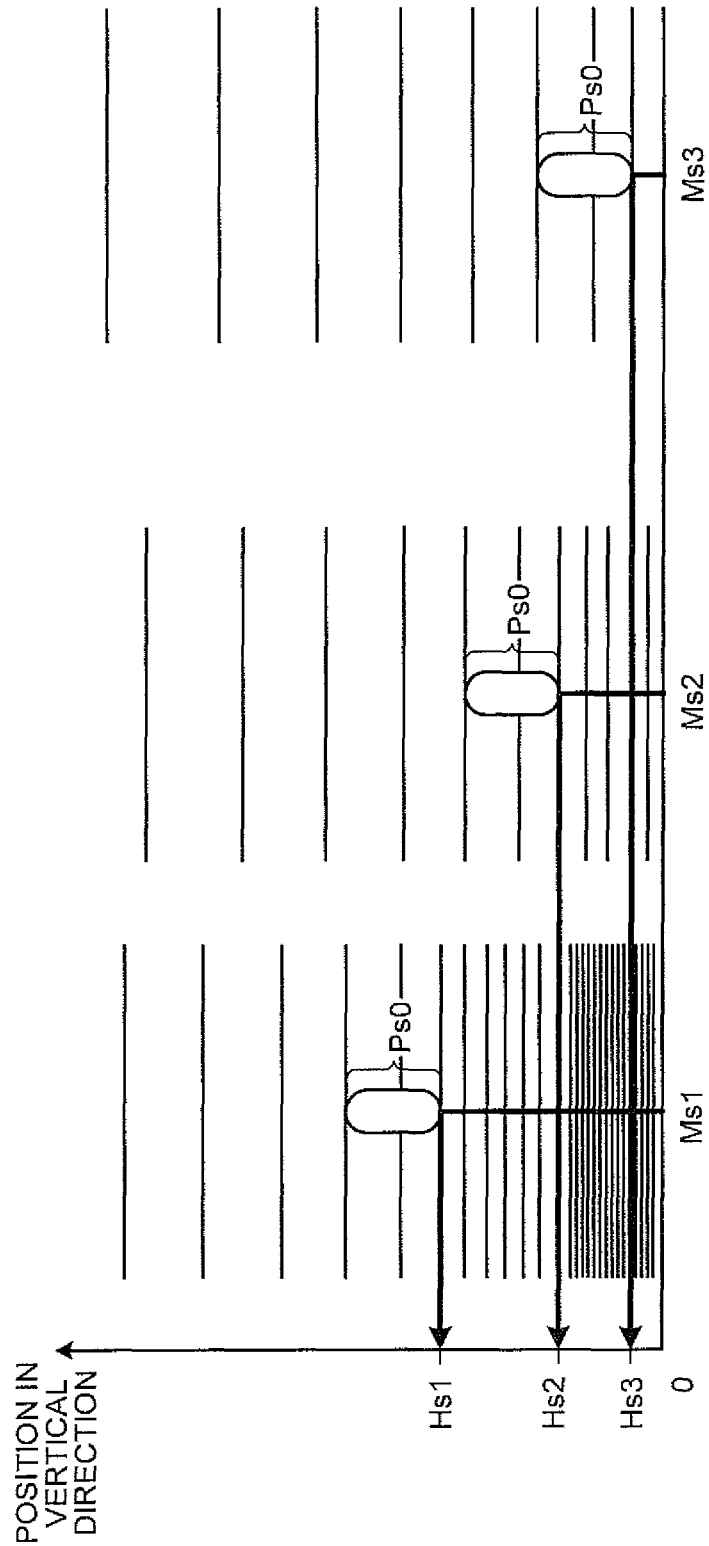
FIG. 6 is an explanatory view of a gradient distribution of a gradient magnetic field to be generated by the magnetic field generator shown in FIG. 1.

Specifically, a sparse-dense pattern Ps0 of magnetic force lines Lg corresponding to the tilt enabling the capsule endoscope 10 to start to move is obtained in advance as shown in FIG. 5. Then, the magnetic field generator 2 is made to generate in stages a gradient magnetic field of a gradient distribution pattern Ms1 in which the sparse-dense pattern Ps0 locates at a position Hs1 in the vertical direction, a gradient magnetic field of a gradient distribution pattern Ms2 in which the sparse-dense pattern Ps0 locates at a position Hs2 in the vertical direction, and a gradient magnetic field of a gradient distribution pattern Ms3 in which the sparse-dense pattern Ps0 locates at a position Hs3 in the vertical direction as shown in FIG. 6. Then, what gradient magnetic field enables the capsule endoscope 10 to start to move among these gradient magnetic fields is confirmed.

The situation in which the capsule endoscope 10 starts to move indicates that the magnetic field having the tilt corresponding to the sparse-dense pattern Ps0 arises at a position where the capsule endoscope 10 locates. This means the position of the tilt corresponding to the sparse-dense pattern Ps0 equals to the position of the capsule endoscope 10. Thus, the position of the capsule endoscope 10 in the vertical direction is obtained by confirming a gradient magnetic field having arisen when the capsule endoscope 10 starts to move and obtaining the position of the sparse-dense pattern Ps0 in this gradient magnetic field in the vertical direction. In FIG. 6, if the capsule endoscope 10 starts to move when the gradient magnetic field of the gradient distribution pattern Ms1 is generated, it is possible to determine that the capsule endoscope 10 locates at the position Hs1 in the vertical direction, if the capsule endoscope 10 starts to move when the gradient magnetic field of the gradient distribution pattern Ms2 is generated, it is possible to determine that the capsule endoscope 10 locates at the position Hs2 in the vertical direction, and if the capsule endoscope 10 starts to move when the gradient magnetic field of the gradient distribution pattern Ms3 is generated, it is possible to determine that the capsule endoscope 10 locates at the position Hs3 in the vertical direction.

Figure 7:
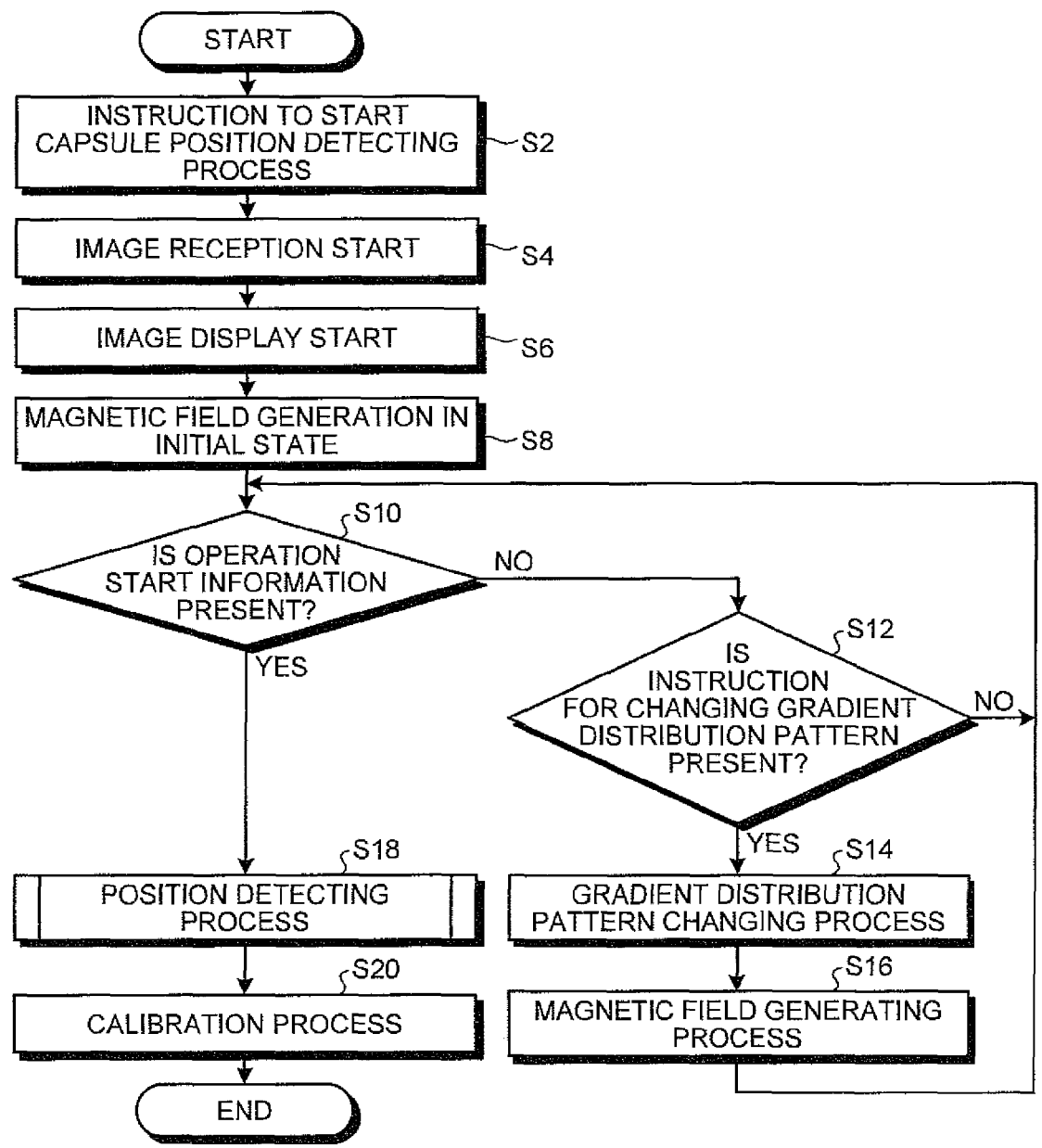
FIG. 7 is a flowchart of a procedure of a calibration process in the capsule medical device guidance system shown in FIG. 1.

In the first embodiment, a calibration process is performed in which a magnetic field is set so that a most suitable magnetic attraction is generated at the position of the capsule endoscope 10 obtained in the manner described above. Then, the calibration process in the capsule medical device guidance system shown in FIG. 1 will be explained next. FIG. 7 is a flowchart of a procedure of the calibration process in the capsule medical device guidance system 1 shown in FIG. 1.

As shown in FIG. 7, as an instruction to start the calibration, instructing information for instructing to start to detect the position of the capsule endoscope 10 is input through the operation input unit 60 to the external control unit 4 (step S2) to start the calibration process.

Figure 8:
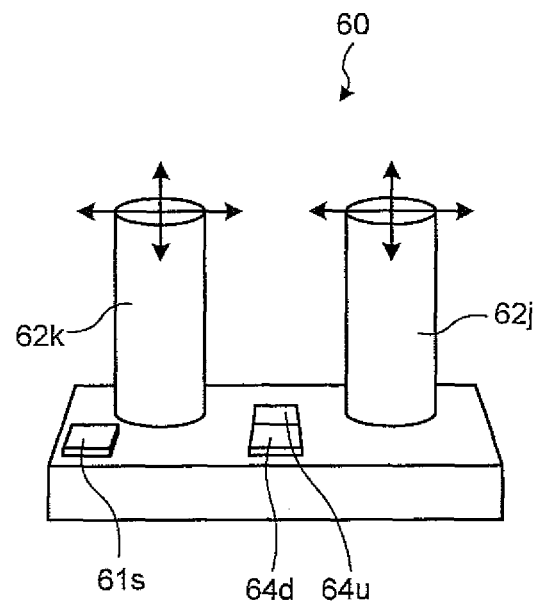
FIG. 8 is a view of an example of the operation input unit shown in FIG. 1.

For example, the operation input unit 60 is constituted by a calibration button 61s, two joysticks 62j and 62k, a gradient up button 64u, and a gradient down button 64d as exemplified in FIG. 8. The calibration button 61s allows, when depressed, inputting the instructing information for instructing to start to detect the position of the capsule endoscope 10 and operation start information indicating that the capsule endoscope 10 starts to move to the external control unit 4. The gradient up button 64u allows, when depressed, inputting to the external control unit 4 gradient pattern up information instructing, as a gradient magnetic field to be generated by the magnetic field generator 2, to generate a gradient magnetic field having a gradient distribution pattern in which the tilt enabling the capsule endoscope 10 to start to move locates at an upper side by one step in the vertical direction compared to the gradient magnetic field generated so far. The gradient down button 64d allows, when depressed, inputting to the external control unit 4 gradient pattern down information instructing, as a gradient magnetic field to be generated by the magnetic field generator 2, to generate a gradient magnetic field having a gradient distribution pattern in which the tilt enabling the capsule endoscope 10 to start to move locates at a lower side by one step in the vertical direction compared to the gradient magnetic field generated so far. The joysticks 62j and 62k are capable of, by being tilted, being operated in the vertical direction and in the horizontal direction, and allow, via the tilt operation in the vertical direction or the horizontal direction, inputting to the external control unit 4 operating information for three-dimensionally operating the magnetic guidance of the capsule endoscope 10 by the magnetic field generator 2.

In the external control unit 4, the image receiver 41 starts an image receiving process of sequentially obtaining in-vivo images that the transceiver 3 has sequentially received (step S4) and the image display controller 42 starts an image displaying process of making the display unit 5 display the in-vivo images that the transceiver 3 has subsequently received (step S6).

The magnetic field control instructing unit 45 makes the magnetic field generator 2 generate a gradient magnetic field in an initial state (step S8). In this case, the magnetic field control instructing unit 45 makes the magnetic field generator 2 generate a gradient magnetic field having a gradient biasing in a direction opposite to a direction of the resultant force of the buoyancy and the gravity of the capsule endoscope 10. The magnetic field control instructing unit 45 makes the magnetic field generator 2 generate a gradient magnetic field for bringing the capsule endoscope 10 in contact with a reference surface in the initial state, the reference surface being at least one of an upper boundary surface and a lower boundary surface of the liquid. A gradient of the gradient magnetic field to be generated by the magnetic field generator 2 in this case varies depending on a position in the vertical direction.

Figure 9:
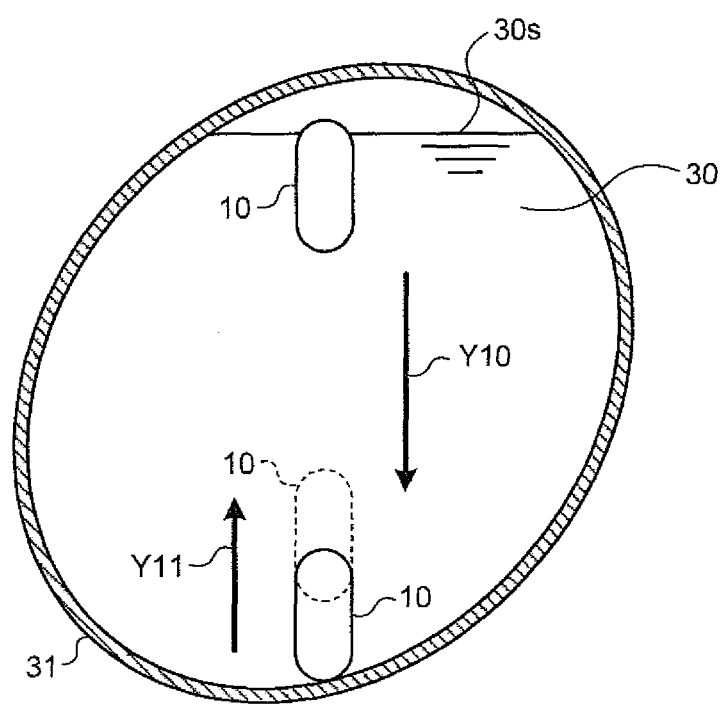
FIG. 9 is an explanatory view of an example of a magnetic guidance of the capsule endoscope on the calibration process according to the first embodiment.

For example, the magnetic field control instructing unit 45 causes a gradient magnetic field providing a downward magnetic attraction sufficiently larger than the upward resultant force of the buoyancy and the gravity of the capsule endoscope 10 to be generated with respect to the capsule endoscope 10 floating on a liquid 30 inside the stomach as shown by an arrow Y10 in FIG. 9, and brings the capsule endoscope 10 in contact, in a manner of being depressed, with a stomach wall 31 on the bottom part which is the lower boundary surface of the liquid 30. The magnetic field control instructing unit 45 then makes the magnetic field generator 2 generate, as the initial state, a gradient magnetic field having a gradient distribution pattern in which the tilt enabling the capsule endoscope 10 to start to move locates at an upper side in the vertical direction from the stomach wall 31 on the bottom part of the stomach in which the capsule endoscope 10 is guided.

The magnetic field control instructing unit 45 then determines whether the operation start information indicating that the capsule endoscope 10 starts to move is input through the input unit 6 (step S10). When determining that the operation start information indicating the capsule endoscope 10 starts to move is not input through the input unit 6 ("No" at step S10), the magnetic field control instructing unit 45 determines whether an instruction of a changed gradient pattern of a gradient magnetic field to be generated next by the magnetic field generator 2 is present (step S12). When determining that the instruction of the changed gradient pattern of the gradient magnetic field is not present ("No" at step S12), the magnetic field control instructing unit 45 returns to step S10 and determines again whether the operation start information is present. On the other hand, when determining that the instruction of the changed gradient pattern of the gradient magnetic field is present ("Yes" at step S12), the magnetic field control instructing unit 45 follows the instruction of the changed gradient pattern, makes a change to a gradient distribution pattern of a gradient magnetic field to be generated by the magnetic field generator 2 (step S14), makes the magnetic field generator 2 generate a gradient magnetic field having a changed gradient distribution pattern (step S16), and then returns to step S10 to determine again whether the operation start information is present.

For example, the case where the floating capsule endoscope 10 is pressed downward against the stomach wall 31 at the bottom side will be taken as an example and explained as shown in FIG. 9. An operator depresses the gradient down button 64d since it is necessary to make the downward magnetic attraction floatage of the capsule endoscope 10 from the stomach wall 31 on the bottom part as shown by an arrow Y11 is not confirmed in the case shown in FIG. 9. Thus, the gradient down button 64d allows inputting gradient pattern down information to the external control unit 4.

The magnetic field control instructing unit 45 makes a change, as a gradient magnetic field to be generated by the magnetic field generator 2, to a gradient magnetic field having a gradient distribution pattern in which the tilt enabling the capsule endoscope 10 to start to move locates at a lower side by one step in the vertical direction compared to the gradient magnetic field generated so far. Specifically, the magnetic field control instructing unit 45 makes the magnetic field generator 2 generate a gradient magnetic field by relaxing a gradient compared to the gradient magnetic field generated so far. In other words, the magnetic field control instructing unit 45 makes the magnetic field generator 2 gradually change the gradient distribution of the gradient magnetic field to generate such that the capsule endoscope 10 is away upward from the stomach wall 31 on the bottom part which is the reference surface.

The magnetic field control instructing unit 45 makes the magnetic field generator 2 generate a gradient magnetic field having the gradient distribution pattern Ms1 shown in FIG. 6 for example as the initial state and generate, when the gradient pattern down information is input in this case, the gradient distribution pattern Ms2 in which the sparse-dense pattern Ps0 corresponding to the tilt enabling the capsule endoscope 10 to start to move locates at a lower side by one step.

Figure 10:
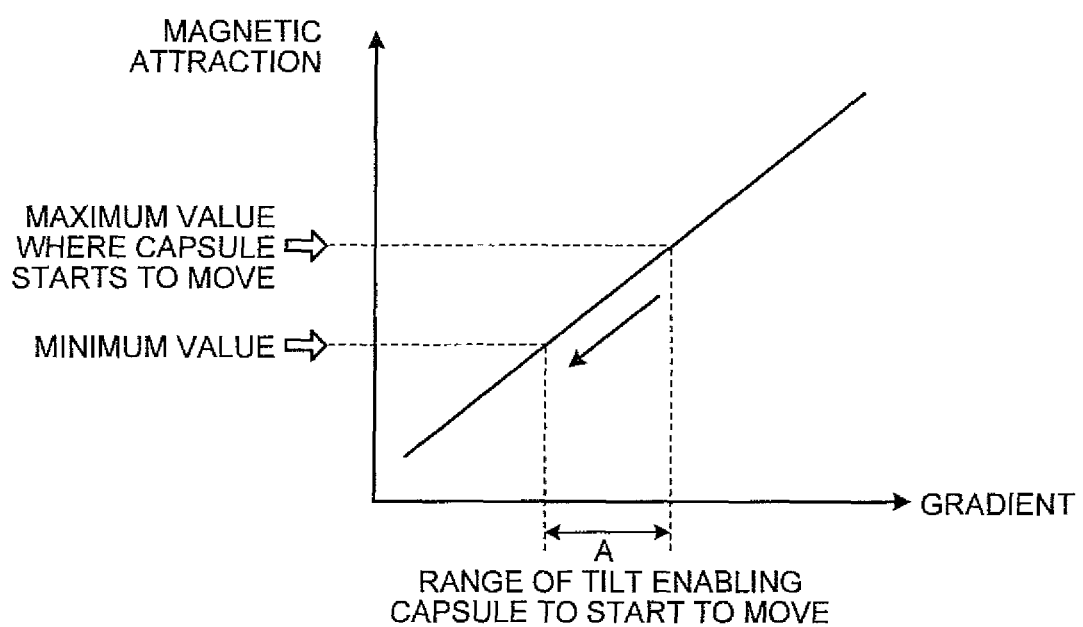
FIG. 10 exemplifies a relation between a gradient and a magnetic attraction.

In this manner, the operator only needs to keep depressing the gradient down button 64d until it is confirmed that the capsule endoscope 10 starts to float. As a result of this, the position of the tilt enabling the capsule endoscope 10 to start to move in the vertical direction becomes gradually lowered. In other words, the downward magnetic attraction acting on the capsule endoscope 10 is weakened by lowering the gradient as shown by an arrow in FIG. 10. Besides, when the capsule endoscope 10 floats up more than expected, the operator only needs to depress the gradient up button 64u to heighten the gradient. The operator again depresses the calibration button 61s shown in FIG. 8 when it is confirmed that the capsule endoscope 10 starts to float from the stomach wall 31 on the bottom part as shown by the arrow Y11 in FIG. 9 via the adjustment by depressing the gradient up button 64u and the gradient down button 64d. As a result of this, the operation start information is input through the operation input unit 60.

When determining that the operation start information indicating that the capsule endoscope 10 starts to move is input through the input unit 6 ("Yes" at step S10), the magnetic field control instructing unit 45 outputs to the position detector 46 information indicating the gradient distribution pattern of the gradient magnetic field generated by the magnetic field generator 2 when the operation start information is input. The position detector 46 performs a position detecting process of detecting the position of the capsule endoscope 10 in the vertical direction based on the gradient distribution pattern of the gradient magnetic field generated by the magnetic field generator 2 when the operation start information is input (step S18).

The magnetic field control instructing unit 45 performs a calibration process in which a magnetic field to be generated by the magnetic field generator 2 is set based on the position of the capsule endoscope 10 in the vertical direction detected by the position detector 46 (step S20) and ends the calibration process.

Figure 11:
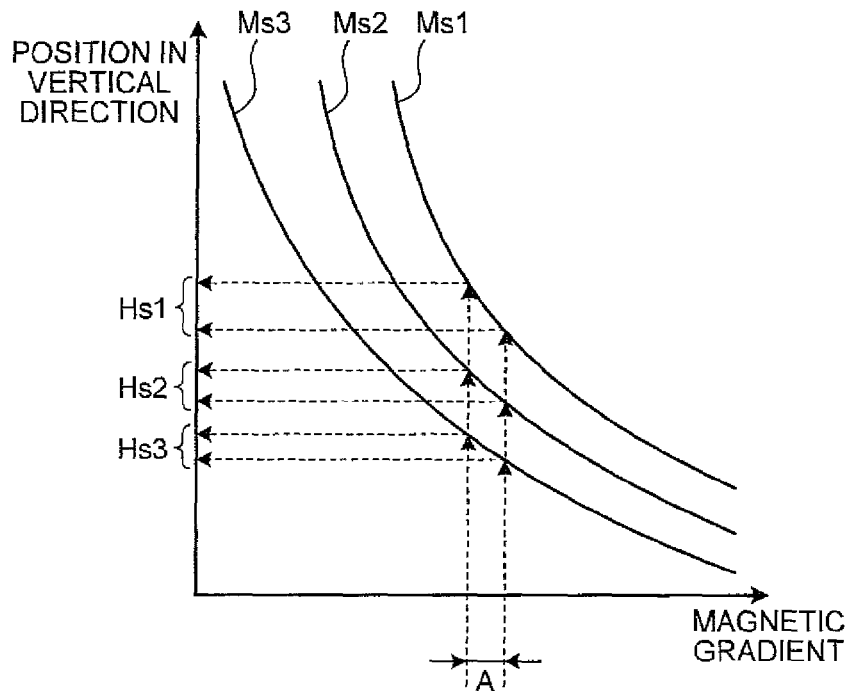
FIG. 11 is an explanatory view of the gradient distribution of the gradient magnetic field to be generated by the magnetic field generator shown in FIG. 1.

Here, the position detector 46 performs the position detecting process based on a correspondence relation in which the position of the tilt enabling the capsule endoscope 10 to start to move in the vertical direction is associated with each gradient magnetic field to be generated by the magnetic field generator. For example, in the case where the magnetic field generator 2 gradually generates the gradient magnetic field of each of the gradient distribution patterns Ms1 to Ms3 shown in FIG. 6, a correspondence relation in which a range A of the tilt enabling the capsule endoscope 10 to start to move is associated with each of the positions Hs1 to Hs3 of the tilt in the vertical direction is obtained in advance for each of the gradient distribution patterns Ms1 to Ms3 as shown in FIG. 11. The position detector 46 detects the position of the capsule endoscope 10 in the vertical direction based on the correspondence relation shown in FIG. 11. In the case of relaxing the gradient of the gradient magnetic field as shown in FIG. 9, the position in the vertical direction in the gradient distribution patterns Ms1 to Ms3 with respect to the range A of the tilt enabling the capsule endoscope 10 to start to move are predetermined since the range A of the gradient in which the capsule endoscope 10 starts to float corresponds to the tilt enabling the capsule endoscope 10 to start to move. As shown FIGS. 10 and 11, the tilt enabling the capsule endoscope 10 to start to move is set to have a width (range A) by taking variation in a physical parameter of the capsule endoscope and a physical parameter of the liquid inside the body into consideration. Here, a representative value (a median, a maximum value, a minimum value, and the like in the range A) may be used to detect the position.

Figure 12:
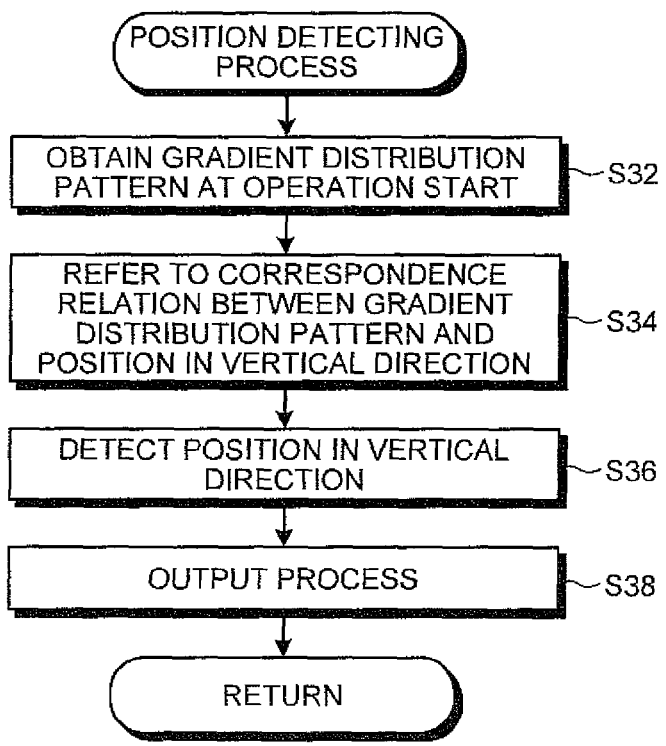
FIG. 12 is a flowchart of a procedure of a position detecting process shown in FIG. 7.

The position detecting process shown in FIG. 7 will be explained with reference to FIG. 12. FIG. 12 is a flowchart of a procedure of the position detecting process shown in FIG. 7. As shown in FIG. 12, the position detector 46 obtains the gradient distribution pattern of the gradient magnetic field generated by the magnetic field generator 2 when the operation start information is input as a gradient distribution pattern at the time of the operation start (step S32). The position detector 46 refers to the correspondence relation between the gradient distribution pattern of each gradient magnetic field to be generated by the magnetic field generator 2 and the position of the tilt in which the capsule endoscope 10 starts to move in the vertical direction (step S34). This correspondence relation is stored in a memory provided in the external control unit 4, for example. Next, the position detector 46 obtains the position of the tilt in which the capsule endoscope 10 starts to move in the vertical direction in the gradient distribution pattern, obtained at step S32, of the gradient magnetic field generated by the magnetic field generator 2 when the operation start information is input based on the correspondence relation of reference and performs a detection by treating the obtained position in the vertical direction as the position of the capsule endoscope 10 in the vertical direction (step S36). Then, the position detector 46 performs an output process in which the obtained position of the capsule endoscope 10 in the vertical direction is output to the magnetic field control instructing unit 45 (step S38) and ends the position detecting process.

The magnetic field control instructing unit 45 then performs the calibration process (step S20) based on the position of the capsule endoscope 10 in the vertical direction detected by the position detector 46. To allow the capsule endoscope 10 to move appropriately inside the organ where the capsule endoscope 10 actually locates, the magnetic field control instructing unit 45 sets a target area in the calibration process (step S20) based on a size of the inside of the organ in which the capsule endoscope 10 actually locates and the position in the vertical direction detected by the position detector 45. The magnetic field control instructing unit 45 performs a setting to make the magnetic field generator 2 generate a most suitable magnetic field for the guidance of the capsule endoscope 10 within the target area.

In the case shown in FIG. 9, the capsule endoscope 10 is practically guided in an upper area from the stomach wall 31 on the bottom part since the movement start of the capsule endoscope 10 corresponds to the floatage start from the stomach wall 31 on the bottom part as the reference surface and the position in a state where the capsule endoscope 10 is in contact with the stomach wall 31 on the bottom part is detected.

The magnetic field control instructing unit 45 then performs setting so that the most suitable magnetic field is generated in an upper area from the actually detected position of the capsule endoscope 10 in the vertical direction. Specifically, the magnetic field control instructing unit 45 makes the magnetic field generator 2 generate a magnetic field most suitable for the guidance of the capsule endoscope 10 in an area at a side of a direction opposite to the reference surface with respect to the position of the capsule endoscope 10 in the vertical direction detected by the position detector 46.

Figure 13:
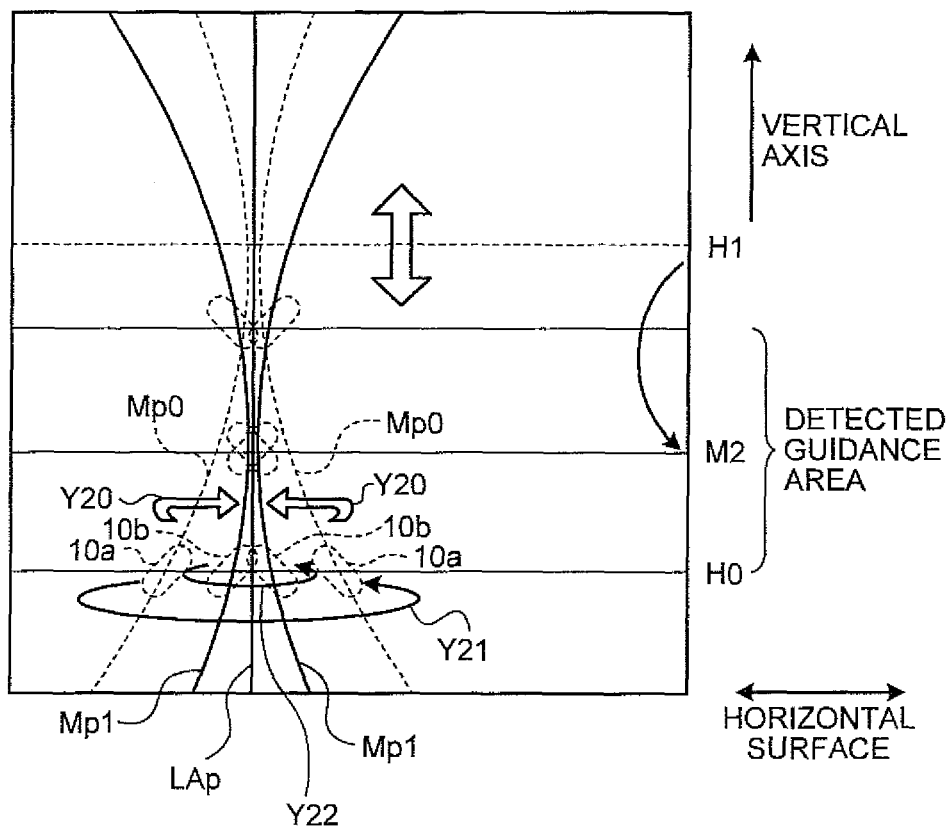
FIG. 13 is an explanatory view of the peak magnetic field to be generated by the magnetic field generator shown in FIG. 1.

A case where the magnetic field control instructing unit 45 performs a most suitable setting concerning a peak magnetic field will be explained. The magnetic field control instructing unit 45 sets a target area based on the position of the capsule endoscope 10 in the vertical direction detected by the position detector 46 and performs a setting so that the magnetic field generator 2 generates a peak magnetic field which aims the target area. FIG. 13 shows a position of the peak magnetic field arising on a surface which becomes parallel to the vertical axis. A case where the capsule endoscope 10 moves in a guidance area M2 shown in FIG. 13 based on a result of the detection by the position detector 46 will be taken as an example and explained. When the magnetic field generator 2 generates a peak magnetic field Mp0 which aims a position H1 which is deviated upward in the vertical axis from the guidance area M2 where the capsule endoscope 10 actually locates, the magnetic field control instructing unit 45 changes the peak magnetic field generated by the magnetic field generator 2 to a peak magnetic field Mp1 which aims a center position of the guidance area M2 as shown by an arrow Y20. Specifically, the magnetic field control instructing unit 45 shifts, by the deviation from the guidance area M2, each peak position of the peak magnetic field Mp0 downward. As shown by the curve lines indicating the respective peak positions of the peak magnetic fields Mp0 and Mp1, the peak of the peak magnetic field does not locate on a vertical axis LAp and shifts in a manner of forming into an arc centering around the vertical axis LAp depending the attitude of the capsule endoscope 10 in the rotating direction when seen on the surface parallel to the vertical axis direction at any time. Thus, the deviation of the peak position in the horizontal direction from the vertical axis LAp in the guidance area M2 is suppressed to a minimum level by setting the peak magnetic field to be generated by the magnetic field generator 2 to the peak magnetic field Mp1, the deviation being caused when the attitude of the capsule endoscope 10 in the rotating direction changes.

In a position H0 which is the lowest end of the guidance area, the former peak magnetic field Mp0 has a peak at a location significantly deviating from the vertical axis LAp in the horizontal direction. In a case of giving an instruction of a rotating operation for causing a rotation on the spot to a capsule endoscope 10a locating on the vertical axis LAp by using the peak magnetic field Mp0, the capsule endoscope 10a is captured at the peak position deviating from the vertical axis LAp due to this peak magnetic field and thereby results in rotating not on the vertical axis LAp but in such a manner as to rotate widely around the vertical axis LAp as shown by an arrow Y21. In contrast, in a case of the newly set peak magnetic field Mp1, the deviation of the peak position from the vertical axis LAp in the horizontal direction is suppressed to the minimum in the guidance area M2. Therefore, in a case of giving an instruction of a rotating operation for causing a rotation on the spot to a capsule endoscope 10b locating on the vertical axis LAp by using the peak magnetic field Mp1, the capsule endoscope 10b is enabled to rotate nearly on the vertical axis LAp as shown by an arrow Y22.

As described, the magnetic field control instructing unit 45 is capable of guiding the capsule endoscope 10 accurately according to the operating information input through the operation input unit 60 since making the magnetic field generator 2 generate a peak magnetic field by aiming the guidance area where the capsule endoscope 10 actually locates.

Figure 14A:
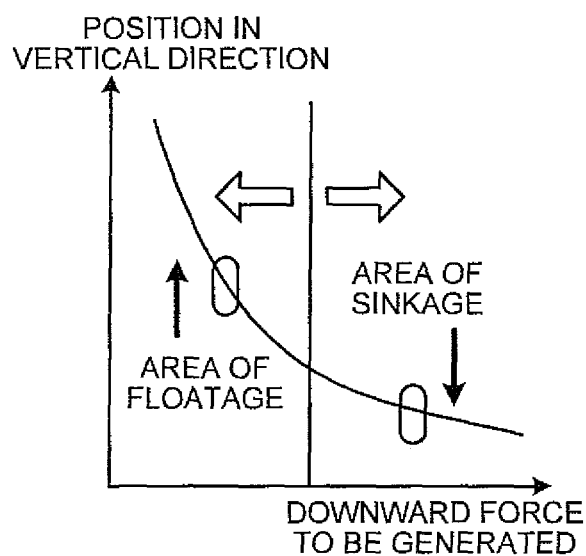
FIGS. 14A and 14B are explanatory views of a magnetic attraction which changes depending on a position at which the capsule endoscope locates in the vertical direction.

The magnetic attraction generated by the magnetic field by the magnetic field generator 2 in the vertical direction varies depending on the position in the vertical direction. Specifically, the vertical magnetic attraction acting on the capsule endoscope 10 differs depending on the position at which the capsule endoscope 10 locates in the vertical direction. Even in the case of generating a magnetic field so that a downward magnetic attraction in the vertical axis arises as shown in FIG. 14A, the downward magnetic attraction acting on the capsule endoscope 10 differs depending on the position of the capsule endoscope 10 in the vertical direction, thereby causing an area in which the capsule endoscope 10 floats and an area in which the capsule endoscope 10 sinks. Conventionally, a magnetic field to be generated would not be adjusted based on the vertical direction of the capsule endoscope 10. In other words, a target area is set uniformly and a magnetic field to be generated is set so that a suitable magnetic attraction arises in the uniformly-set area conventionally. Therefore, if the capsule endoscope is indeed deviated from the target area in the vertical direction, there is a case where a magnetic attraction necessary for causing the sinkage does not work on the capsule endoscope, which results in a failure in causing the capsule endoscope 10 to sink even when the operator performs an operation of causing the capsule endoscope to sink.

In the first embodiment, the position of the capsule endoscope 10 in the vertical direction is detected and a magnetic field is generated so that a magnetic attraction responding to an operation of the operation input unit 60 properly works in an area in which the capsule endoscope 10 actually moves. Therefore, when the operator performs an operation of causing the capsule endoscope 10 to sink, it is possible to cause the capsule endoscope 10 to sink in accordance with the instruction from the operator since a magnetic field is generated so that the area where the capsule endoscope 10 actually locates is aimed and a magnetic attraction necessary for the sinkage is made to act on the capsule endoscope 10 in the first embodiment. Thus, it is possible according to the first embodiment to cause the capsule endoscope 10 to properly move in response to the guidance operation instructed by the operator.

Figure 14B:
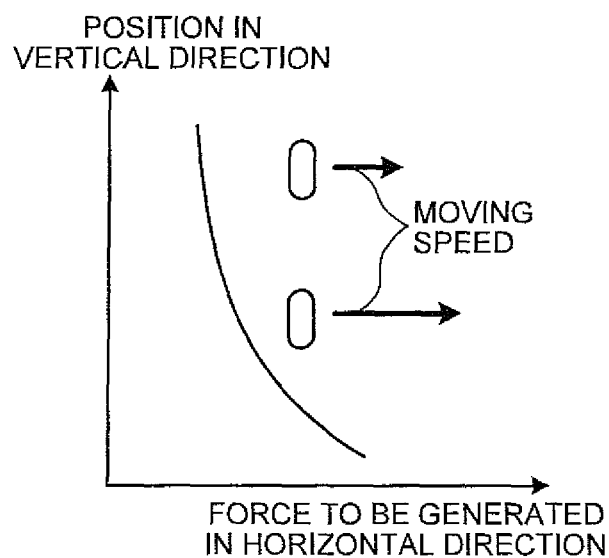

The gradient of the magnetic field to be generated by the magnetic field generator 2 differs depending on the position in the vertical direction as described. Therefore, the magnetic attraction arising by the magnetic field generated by the magnetic field generator 2 in the horizontal direction differs and a moving speed of the capsule endoscope 10 in the horizontal direction also differs depending on the position in the horizontal direction when a magnetic field is generated so that a horizontal magnetic attraction arises as shown in FIG. 14B. Since the position of the capsule endoscope 10 in the vertical direction is detected and a magnetic field is generated so that a magnetic attraction responding to an operation of the operation input unit 60 properly works in an area in which the capsule endoscope 10 actually moves in the first embodiment, it is possible to make the capsule endoscope 10 move at a guidance speed instructed by the operator and thereby improve the operability.

Here, while the case of generating a gradient magnetic field which provides a downward magnetic attraction to the capsule endoscope 10 floating on the liquid 30 inside the stomach and bringing the capsule endoscope 10 in contact, in a manner of being depressed, with the stomach wall 31 on the bottom part which is the lower boundary surface of the liquid 30 as shown in FIG. 9 is explained as the initial state in FIG. 7, the present invention is not limited thereto and a case of bringing the floating capsule endoscope 10 in contact with a liquid surface 30s which is the upper boundary surface may be set as the initial state.

Figure 15:
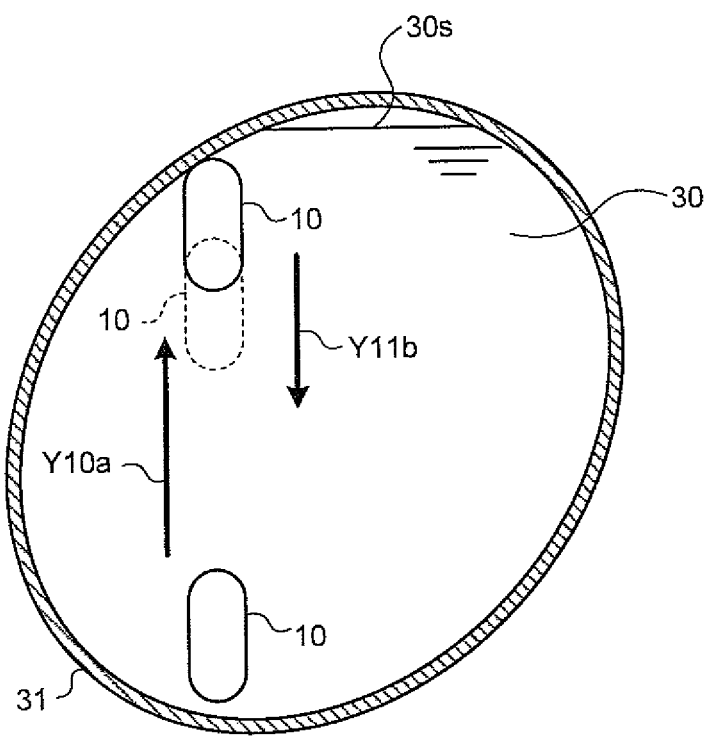
FIG. 15 is an explanatory view of another example of the magnetic guidance of the capsule endoscope on the calibration process according to the first embodiment.

In this case, the magnetic field control instructing unit 45 makes the magnetic field generator 2 generate a gradient magnetic field providing a downward or an upward magnetic attraction sufficiently smaller than the upward resultant force of the buoyancy and the gravity of the capsule endoscope 10 to the capsule endoscope 10 floating on the liquid 30 inside the stomach as shown by an arrow Y10a in FIG. 15 at step S2 in FIG. 7, and brings the capsule endoscope 10 in contact with the liquid surface 30s which is the upper boundary surface of the liquid 30. Specifically, the magnetic field control instructing unit 45 makes the magnetic field generator 2 generate, as the initial state, a gradient magnetic field having a gradient distribution pattern in which the tilt enabling the capsule endoscope 10 to start to move locates at a lower side in the vertical direction from the liquid surface 30s in the stomach.

In the case shown in FIG. 15, the operator depresses the gradient up button 64u since the downward magnetic attraction is required to be made large to cause the capsule endoscope 10 to sink when the sinkage of the capsule endoscope 10 from the liquid surface 30s as shown by an arrow Y11 in FIG. 9 cannot be confirmed. Thus, the gradient up button 64u allows inputting gradient pattern up information to the external control unit 4 ("Yes" at step S12). As a result of this, the magnetic field control instructing unit 45 makes a change, as a gradient magnetic field to be generated by the magnetic field generator 2, to a gradient magnetic field having a gradient distribution pattern in which the tilt enabling the capsule endoscope 10 to start to move locates at an upper side by one step in the vertical direction compared to the gradient magnetic field generated so far (step S14). As a result of this, the magnetic field generator 2 is made to generate a gradient magnetic field having a higher gradient than the gradient magnetic field generated so far (step S16). In other words, the magnetic field control instructing unit 45 makes the magnetic field generator 2 gradually change the gradient distribution of the gradient magnetic field to generate such that the capsule endoscope 10 is away downward from the liquid surface 30s which is the reference surface.

In this manner, the operator only needs to keep depressing the gradient up button 64u until it is confirmed that the capsule endoscope starts to sink. As a result of this, the position of the tilt enabling the capsule endoscope 10 to start to move in the vertical direction is gradually heightened. The operator again depresses the calibration button 61s shown in FIG. 8 when it is confirmed that the capsule endoscope 10 starts to sink from the liquid surface 30s as shown by the arrow Y11b in FIG. 15. As a result of this, the operation start information is input from the operation input unit 60.

The magnetic field generator 2 may eliminate an influence of a surface tension of the capsule endoscope 10 by making the magnetic field generator 2 temporarily generate a magnetic field having a high intensity which can counteract the surface tension on the liquid surface and then generate a magnetic field corresponding to the operating instruction of the gradient up button 64u and the gradient down button 64d. In this case, the magnetic field generator 2 is made to temporarily generate a downward magnetic field having a high intensity in the vertical direction to cause the capsule endoscope 10 to move from the liquid surface 30s into the liquid 30. Besides, the magnetic field generator 2 may be made to generate a magnetic field which causes a tilting operation at high speed to make the attitude of the capsule endoscope 10 change at high speed. In this case, a side wall of the capsule endoscope 10 exposed from the liquid surface 30s is soused with the liquid by the tilting operation, so that the influence of the surface tension is eliminated.

The position detector 46 then performs the position detecting process of detecting the position of the capsule endoscope 10 in the vertical direction based on the gradient distribution pattern of the gradient magnetic field generated by the magnetic field generator 2 when the operation start information is input (step S18) and the magnetic field control instructing unit 45 performs the calibration process (step S20). In the case shown in FIG. 15, the capsule endoscope 10 is practically guided in a lower area from the liquid surface 30s since the movement start of the capsule endoscope 10 corresponds to the sinkage start from the liquid surface 30s as the reference surface. Therefore, the magnetic field control instructing unit 45 makes the magnetic field generator 2 generate a magnetic field most suitable for the guidance of the capsule endoscope 10 in a lower area at a side opposite to the reference surface with respect to the position of the capsule endoscope 10 in the vertical direction detected by the position detector 46.

Besides, while the capsule endoscope 10 floating on the liquid 30 is taken as an example and explained in the first embodiment, the present invention can be applied to a case of using a capsule endoscope which sinks in the liquid. In the case where the stomach wall 31 on the bottom part is the reference surface, the magnetic field control instructing unit 45 makes the magnetic field generator 2 generate a gradient magnetic field which provides an upward or a downward magnetic attraction sufficiently smaller than the downward resultant force of the buoyancy and the gravity of the capsule endoscope to the capsule endoscope sinking in the liquid inside the stomach at step S2 in FIG. 7, and brings the capsule endoscope in contact with the stomach wall 31 on the bottom part. Specifically, the magnetic field control instructing unit 45 makes the magnetic field generator 2 generate, as the initial state, a gradient magnetic field having a gradient distribution pattern in which the tilt enabling the capsule endoscope to start to move locates at a lower side in the vertical direction from the stomach wall 31 on the bottom part.

The operator then depresses the gradient up button 64u since it is necessary to make the upward magnetic attraction large so that the capsule endoscope floats up when the floatage from the stomach wall on the bottom part as shown by the arrow Y11b is not confirmed. Thus, the gradient up button 64u allows inputting gradient pattern up information to the external control unit 4 ("Yes" at step S12) and the magnetic field control instructing unit 45 makes a change, as a gradient magnetic field to be generated by the magnetic field generator 2, to a gradient magnetic field having a gradient distribution pattern in which the tilt enabling the capsule endoscope to start to move locates at an upper side by one step in the vertical direction compared to the gradient magnetic field generated so far (step S14). Then, the magnetic field control instructing unit 45 makes the magnetic field generator 2 generate a gradient magnetic field having a higher gradient than the gradient magnetic field generated so far (step S16).

In this manner, the operator only needs to keep depressing the gradient up button 64u until it is confirmed that the capsule endoscope starts to float. As a result of this, the position of the tilt enabling the capsule endoscope to start to move in the vertical direction becomes gradually heightened. The operator again depresses the calibration button 61s shown in FIG. 8 when it is confirmed that the capsule endoscope starts to float from the stomach wall 31 on the bottom part. As a result of this, the operation start information is input through the operation input unit 60. The position detector 46 then performs the position detecting process of detecting the position of the capsule endoscope in the vertical direction based on the gradient distribution pattern of the gradient magnetic field generated by the magnetic field generator 2 when the operation start information is input (step S18) and the magnetic field control instructing unit 45 performs the calibration process (step S20). In this case, the capsule endoscope is practically guided in an upper area from the stomach wall 31 on the bottom part since the movement start of the capsule endoscope corresponds to the floatage start from the stomach wall 31 on the bottom part as the reference surface. Therefore, the magnetic field control instructing unit 45 makes the magnetic field generator 2 generate a magnetic field most suitable for the guidance of the capsule endoscope 10 in an upper area at a side opposite to the reference surface with respect to the position of the capsule endoscope in the vertical direction detected by the position detector 46.

Besides, a case of bringing the capsule endoscope to sink in contact with the liquid surface 30s on the upper boundary surface may be set as the initial state. In this case, the magnetic field control instructing unit 45 makes the magnetic field generator 2 generate a gradient magnetic field which provides an upward magnetic attraction sufficiently larger than the downward resultant force of the buoyancy and the gravity of the capsule endoscope to the capsule endoscope which sinks in the liquid 30 at step S2 in FIG. 7, and brings the capsule endoscope in contact with the liquid surface as the upper boundary surface of the liquid. Specifically, the magnetic field control instructing unit 45 makes the magnetic field generator 2 generate, as the initial state, a gradient magnetic field having a gradient distribution pattern in which the tilt enabling the capsule endoscope to start to move locates at an upper side in the vertical direction from the liquid surface where the capsule endoscope is guided.

The operator depresses the gradient down button 64d since it is necessary to make the upward magnetic attraction small so that the capsule endoscope sinks down when it is not confirmed that the capsule endoscope sinks down from the liquid surface 30s. Thus, the gradient down button 64d allows inputting gradient pattern down information to the external control unit 4 ("Yes" at step S12). As a result of this, the magnetic field control instructing unit 45 makes a change, as a gradient magnetic field to be generated by the magnetic field generator 2, to a gradient magnetic field having a gradient distribution pattern in which the tilt enabling the capsule endoscope to start to move locates at a lower side by one step in the vertical direction compared to the gradient magnetic field generated so far (step S14). As a result of this, the magnetic field generator 2 is made to generate a gradient magnetic field having a lower gradient than the gradient magnetic field generated so far (step S16). In other words, the magnetic field control instructing unit 45 makes the magnetic field generator 2 gradually change the gradient distribution of the gradient magnetic field to generate such that the capsule endoscope is away downward from the liquid surface 30s as the reference surface.

In this manner, the operator only needs to keep depressing the gradient down button 64d until it is confirmed that the capsule endoscope starts to sink. As a result of this, the position of the tilt enabling the capsule endoscope to start to move in the vertical direction becomes gradually lowered. The operator again depresses the calibration button 61s shown in FIG. 8 when it is confirmed that the capsule endoscope starts to sink from the liquid surface. As a result of this, the operation start information is input through the operation input unit 60. The magnetic field generator 2 may eliminate an influence of a surface tension of the capsule endoscope by making the magnetic field generator 2 temporarily generate a magnetic field having a high intensity which can counteract the surface tension on the liquid surface and then generate a magnetic field corresponding to the operating instruction of the gradient up button 64u and the gradient down button 64d.

The position detector 46 then performs the position detecting process of detecting the position of the capsule endoscope in the vertical direction based on the gradient distribution pattern of the gradient magnetic field generated by the magnetic field generator 2 when the operation start information is input (step S18) and the magnetic field control instructing unit 45 performs the calibration process (step S20). In this case, the capsule endoscope is practically guided in a lower area from the liquid surface since the movement start of the capsule endoscope corresponds to the sinkage start from the liquid surface as the reference surface. Therefore, the magnetic field control instructing unit 45 makes the magnetic field generator 2 generate a magnetic field most suitable for the guidance of the capsule endoscope 10 in a lower area at a side opposite to the reference surface with respect to the position of the capsule endoscope in the vertical direction detected by the position detector 46.

If a stable area of the magnetic field is narrow, there is a case where the position of the capsule endoscope 10 in the vertical direction set via the calibration process is different from the actual position of the capsule endoscope 10 in the vertical direction. In this case, the operator may perform a fine adjustment of the area in which the magnetic field is generated by depressing the gradient up button 64u and the gradient down button 64d when recognizing that the position of the capsule endoscope 10 in the vertical direction set in the calibration process is different from the actual position of the capsule endoscope 10 in the vertical direction depending on a degree of a positional change of the capsule endoscope 10 at the time of a rotating instruction.

Besides, the setting for the magnetic field generation in the magnetic field generator 2 may be returned to a calibrated state when the calibration button 61s is depressed for a certain period of time. When the calibration position is significantly deviated by the adjustment via the depression of the gradient up button 64u and the gradient down button 64d, the operator is allowed to make the setting for the magnetic field generation in the magnetic field generator 2 return to the calibrated state by keeping depressing the calibration button 61s for not less than a certain period of time. Or, the setting may be reset to a so-called default state before the start of the calibration when the calibration button 61s is depressed for a certain period of time.

In addition, both of the position detection on the lower boundary surface of the liquid 30 shown in FIG. 9 and the position detection on the upper boundary surface of the liquid 30 shown in FIG. 15 may be performed. On this occasion, the magnetic field control instructing unit 45 makes the magnetic field generator 2 generate a magnetic field most suitable for the guidance of the capsule endoscope 10 between the position obtained by the position detection on the lower boundary surface of the liquid 30 and the position obtained by the position detection on the upper boundary surface of the liquid 30.

At this time, it is possible to grasp an upper limit and a lower limit of the area where the capsule endoscope 10 is present. Thus, it is possible to accurately grasp the guidance area and apply a more suitable magnetic field to the capsule endoscope 10, thereby enhancing a guidance performance.

Second Embodiment

A second embodiment will be explained next. In the second embodiment, a function of detecting an operation of the capsule endoscope 10 is added and a process of detecting the position of the capsule endoscope 10 is performed by determining whether the capsule endoscope 10 starts to move based on a result of the operation detection.

Figure 16:
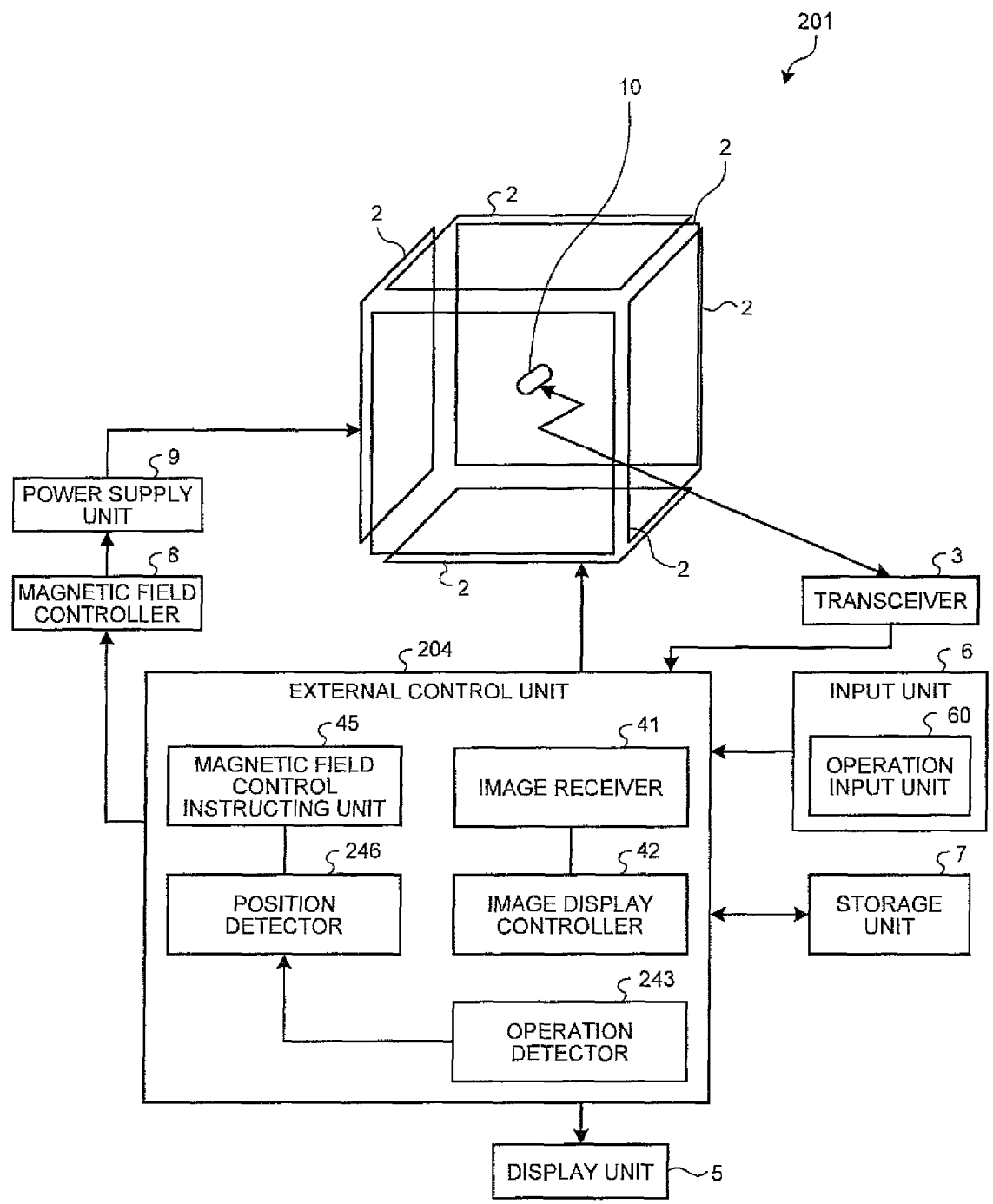
FIG. 16 is a view of an entire structure of a capsule medical device guidance system according to a second embodiment.

FIG. 16 is a view of an entire structure of a capsule medical device guidance system according to the second embodiment. As shown in FIG. 16, a capsule medical device guidance system 201 according to the second embodiment is provided with an external control unit 204 instead of the external control unit 4 shown in FIG. 1. Compared to the external control unit 4 shown in FIG. 1, the external control unit 204 is further provided with an operation detector 243. Besides, the external control unit 204 is provided with, instead of the position detector 46, a position detector 246 that detects a position of the capsule endoscope 10 in the vertical direction based on an operation result of the operation detector 243 compared to the external control unit 4 shown in FIG. 1.

The operation detector 243 detects the operation of the capsule endoscope 10. The operation detector 243 detects the operation of the capsule endoscope 10 inside the subject based on data transmitted from the capsule endoscope 10 to the transceiver 3. For example, the operation detector 243 analyzes images inside the subject transmitted from the capsule endoscope 10 to detect the operation of the capsule endoscope 10. Besides, the operation detector 243 may continuously detect a receiving electric field intensity of the signal transmitted from the capsule endoscope 10 and detect the operation of the capsule endoscope 10 based on a change in the receiving electric field intensity of the signal. For example, the operation detector 243 detects an operation speed of the capsule endoscope 10 inside the subject.

The position detector 246 determines whether the capsule endoscope 10 starts to move based on a result of the detection by the operation detector 243, obtains the gradient distribution of the gradient magnetic field generated by the magnetic field generator 2 when determining that the capsule endoscope 10 starts to move as a gradient distribution pattern at an operation start time, and detects the position of the capsule endoscope 10 in the vertical direction.

Figure 17:
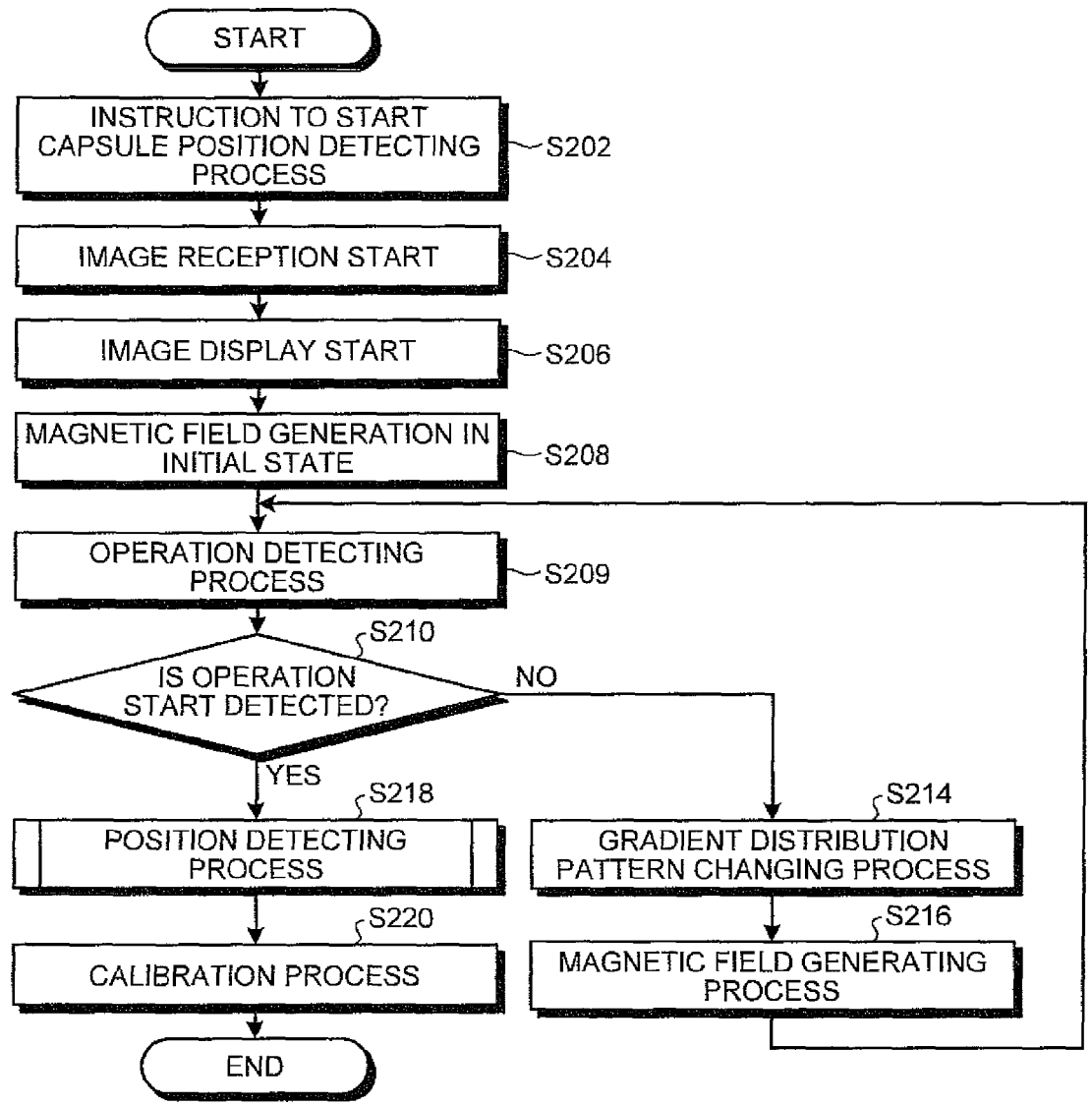
FIG. 17 is a flowchart of a procedure of a calibration process in the capsule medical device guidance system shown in FIG. 16.

Next, a calibration process in the capsule medical device guidance system 201 shown in FIG. 16 will be explained. FIG. 17 is a flowchart of a procedure of the calibration process in the capsule medical device guidance system shown in FIG. 16.

As shown in FIG. 17, a start of the detection of the position of the capsule endoscope 10 is instructed (step S202), the image receiving process by the image receiver 41 is started (step S204), and the image displaying process by the image display controller 42 is started (step S206). Then, the magnetic field control instructing unit 45 makes the magnetic field generator 2 generate a gradient magnetic field in an initial state (step S208).

Next, the operation detector 243 performs an operation detecting process of detecting an operation speed of the capsule endoscope 10 inside the subject based on the data transmitted from the capsule endoscope 10 to the transceiver 3 (step S209) and outputs an operation detection result to the position detector 246.

The position detector 246 determines whether the operation start of the capsule endoscope 10 is detected based on the operation detection result obtained by the operation detector 243 (step S210). When determining that the operation start of the capsule endoscope 10 is not detected ("No" at step S210), the magnetic field control instructing unit 45 changes a gradient distribution pattern of a gradient magnetic field to be generated by the magnetic field generator 2 by one step (step S214), makes the magnetic field generator 2 generate a gradient magnetic field having a changed gradient distribution pattern (step S216), and then returns to step S209.

When determining that the operation start of the capsule endoscope 10 is detected based on the operation detection result obtained by the operation detector 243 ("Yes" at step S210), the position detector 246 obtains information indicating the gradient distribution pattern of the gradient magnetic field generated by the magnetic field generator 2 from the magnetic field control instructing unit 45 and performs the position detecting process of detecting the position of the capsule endoscope 10 in the vertical direction similarly to step S18 shown in FIG. 7 (step S218). Then, the magnetic field control instructing unit 45 performs, similarly to step S20 shown in FIG. 7, the calibration process of setting a magnetic field to be generated by the magnetic field generator 2 based on the position of the capsule endoscope 10 in the vertical direction detected by the position detector 46 (step S220) and ends the calibration process.

In this manner, since one depression of the calibration button 61s by the operator allows automatically performing the position detecting process and the calibration process via the detection of the operation start of the capsule endoscope 10 based on the operation detection result obtained by the operation detector 243, it is possible to simplify the operating process by the operator and to enhance the operability in the second embodiment.

In the second embodiment, the capsule endoscope 10 may be provided with an acceleration sensor and the operation detector 243 may detect the operation speed of the capsule endoscope 10 based on acceleration information obtained from the acceleration sensor of the capsule endoscope 10.

Figure 18A:
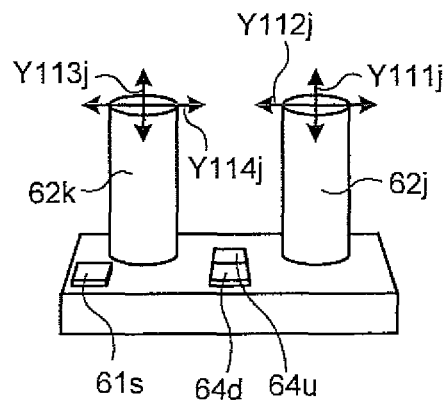
FIG. 18A is a front view of the operation input unit shown in FIG. 8.
Figure 18A:
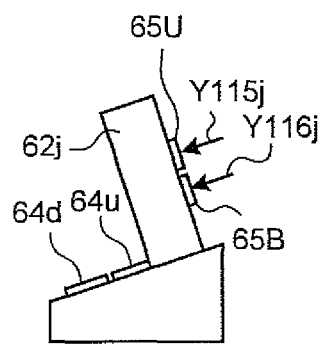

A movement of the capsule endoscope 10 in response to the guidance operation of the operation input unit 60 shown in FIG. 8 will be explained. FIG. 18A is a front view of the operation input unit 60, FIG. 18B is a right side view of the operation input unit 60, and FIG. 18C is a view of the operation of the capsule endoscope 10 instructed by an operation of each component of the operation input unit 60.

Figure 18C:
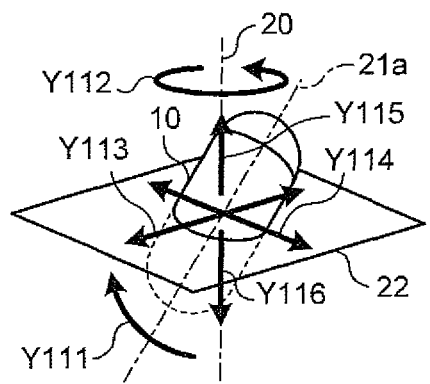
FIG. 18C is a view of an operation of the capsule endoscope instructed by an operation of each component of the operation input unit shown in FIG. 18A.

As shown in FIG. 18A, a vertical tilting direction shown by an arrow Y111$j$ of the joystick 62$j$ corresponds to a direction of the tilting operation in which a head of the capsule endoscope 10 is shaken in a manner of running through a vertical axis 20 as shown by an arrow Y111 in FIG. 18C. When operating information corresponding to the tilting operation of the arrow Y111$j$ of the joystick 62$j$ is input from the operation input unit 60 to the external control units 4 and 204, the magnetic field control instructing unit 45 calculates a guidance direction of the head of the capsule endoscope 10 on the absolute coordinate system in response to the tilting direction of the joystick 62$j$ and calculates a guidance speed in response to the tilting operation of the joystick 62$j$ based on the operating information. The magnetic field control instructing unit 45 then makes the magnetic field generator 2 generate a peak magnetic field in a direction corresponding to the calculated guidance direction, for example and change an angle formed by the direction of the peak magnetic field and the vertical axis 20 at the calculated guidance speed on the vertical surface including the vertical axis 20 and the long axis 21$a$ of the capsule endoscope 10.

As shown in FIG. 18A, a horizontal tilting direction shown by an arrow Y112$j$ of the joystick 62$j$ corresponds to a direction of the rotating operation in which the capsule endoscope 10 rotates centering around the vertical axis 20 as shown by an arrow Y112 in FIG. 18C. When operating information corresponding to the tilting operation of the arrow Y112$j$ of the joystick 62$j$ is input from the operation input unit 60 to the external control units 4 and 204, the magnetic field control instructing unit 45 calculates a guidance direction of the head of the capsule endoscope 10 on the absolute coordinate system in response to the tilting direction of the joystick 62$j$, calculates a guidance speed in response to the tilting operation of the joystick 62$j$, makes the magnetic field generator 2 generate a peak magnetic field in a direction corresponding to the calculated guidance direction, for example, and causes the direction of the peak magnetic field to rotationally move centering around the vertical axis 20 at the calculated guidance speed based on the operating information.

As shown in FIG. 18A, a vertical tilting direction shown by an arrow Y113$j$ of the joystick 62$k$ corresponds to a direction of a horizontal backward operation or a direction of a horizontal forward operation, the both operations moving toward a direction to which the long axis 21$a$ of the capsule endoscope 10 is projected on a horizontal surface 22 as shown by an arrow Y113 in FIG. 18C. When operating information corresponding to the tilting operation of the arrow Y113$j$ of the joystick 62$k$ is input from the operation input unit 60 to the external control units 4 and 204, the magnetic field control instructing unit 45 calculates a guidance direction and a guidance position of the head of the capsule endoscope 10 on the absolute coordinate system in response to the tilting direction of the joystick 62$k$, calculates a guidance speed in response to the tilting operation of the joystick 62$k$, makes the magnetic field generator 2 generate a peak magnetic field in a direction corresponding to the calculated guidance direction, for example, and makes the peak of the peak magnetic field move to the guidance position at the calculated guidance speed based on the operating information.

As shown in FIG. 18A, a horizontal tilting direction shown by an arrow Y114$j$ of the joystick 62$k$ corresponds to a direction of a horizontal right operation or a direction of a horizontal left operation, the both operations allowing the capsule endoscope 10 to move on the horizontal surface 22 perpendicularly to the direction to which the long axis 21*a* is projected on the horizontal surface 22 as shown by an arrow Y114 in FIG. 18C. When operating information corresponding to the tilting operation of the arrow Y114*j* of the joystick 62*k* is input from the operation input unit 60 to the external control units 4 and 204, the magnetic field control instructing unit 45 calculates a guidance direction and a guidance position of the head of the capsule endoscope 10 on the absolute coordinate system in response to the tilting direction of the joystick 62*k*, calculates a guidance speed in response to the tilting operation of the joystick 62*k*, makes the magnetic field generator 2 generate a peak magnetic field in a direction corresponding to the calculated guidance direction, for example, and makes the peak of the peak magnetic field move to the guidance position at the calculated guidance speed based on the operating information.

Besides, an up button 65U and a down button 65B are provided on a back surface of the joystick 62*k*. An up operation of moving upward as shown by an arrow Y115 along the vertical axis 20 shown in FIG. 18C is instructed when the up button 65U is depressed as shown by an arrow Y115*j* in FIG. 18B. A down operation of moving downward as shown by an arrow Y116 along the vertical axis 20 shown in FIG. 18C is instructed when the down button 65B is depressed as shown by an arrow Y116*j* in FIG. 18B. Operating information corresponding to each depression operation of the arrows Y115*j* and Y116*j* respectively of the up button 65U and the down button 65B is input from the operation input unit 60 to the external control units 4 and 204, the magnetic field control instructing unit 45 calculates an operation direction, in response to the depression of either of the up and down buttons, of the head of the capsule endoscope 10 on the absolute coordinate system and makes the magnetic field generator 2 generate a gradient magnetic field having a gradient along the vertical axis 20 in response to the calculated operation direction based on the operating information. When the up button 65U is depressed, the magnetic field generator 2 generates a gradient magnetic field in which a gradient becomes denser toward the upper direction of the vertical axis 20 to allow the capsule endoscope 10 to move as shown by the arrow Y115. When the down button 65B is depressed, the magnetic field generator 2 generates a gradient magnetic field in which a gradient becomes denser toward the lower direction of the vertical axis 20 to allow the capsule endoscope 10 to move as shown by the arrow Y116.

Figure 19:
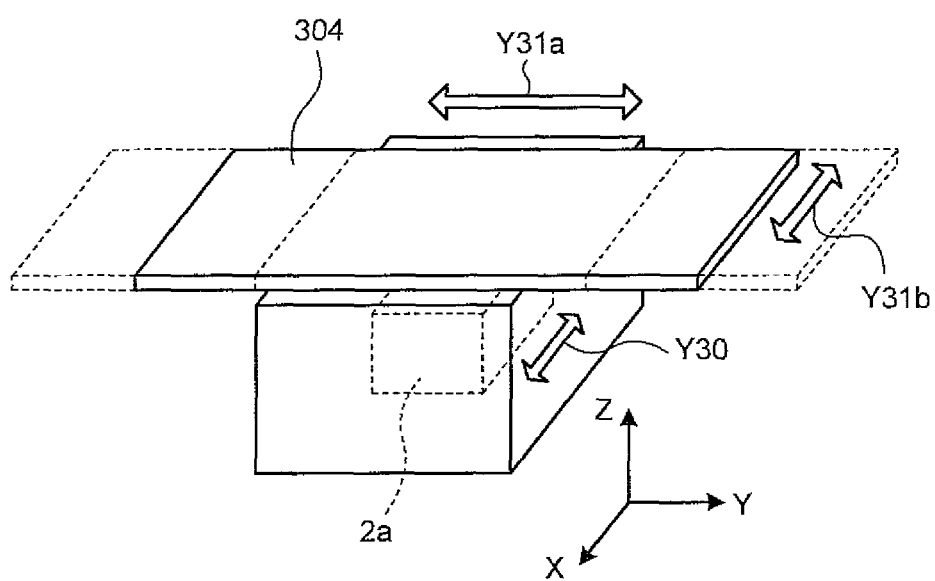
FIG. 19 is a view of an example of a shifting state of a table part of a bed and a shifting state of the magnetic field generator, the bed and the magnetic field generator constituting the capsule medical device guidance system according to the present invention.

In the first and the second embodiments, the peak magnetic field may be shifted inside the subject by changing a relative position between a bed 304 which supports a patient as the subject and a magnetic field generator 2*a* that generates a peak magnetic field on the central axis as shown in FIG. 19. FIG. 19 is a view of an example of a shifting state of a table part of the bed 304 and a shifting state of the magnetic field generator. As shown in FIG. 19, the bed 304 can be horizontally shifted in the Y axis direction of the absolute coordinate system as shown by an arrow Y31*a* and the magnetic field generator 2*a* can be horizontally shifted in the X axis direction of the absolute coordinate system as shown by an arrow Y30, for example. In this case, the relative position between the bed 304 and the magnetic field generator 2*a* is changed by shifting the bed 304 and the magnetic field generator 2*a* and a peak magnetic field having a peak at a predetermined position on the horizontal surface is generated. If the bed 304 can be shifted in the X axis direction of the absolute coordinate system as shown by an arrow Y31*b* in addition to the Y axis direction of the absolute coordinate system, the relative position between the bed 304 and the magnetic field generator 2*a* may be changed by shifting the bed 304 only. Besides, if the magnetic field generator 2*a* can be shifted in the Y axis direction of the absolute coordinate system in addition to the X axis direction on the absolute coordinate system, the relative position between the bed 304 and the magnetic field generator 2*a* may be changed by shifting the magnetic field generator 2*a* only.

Figure 20:
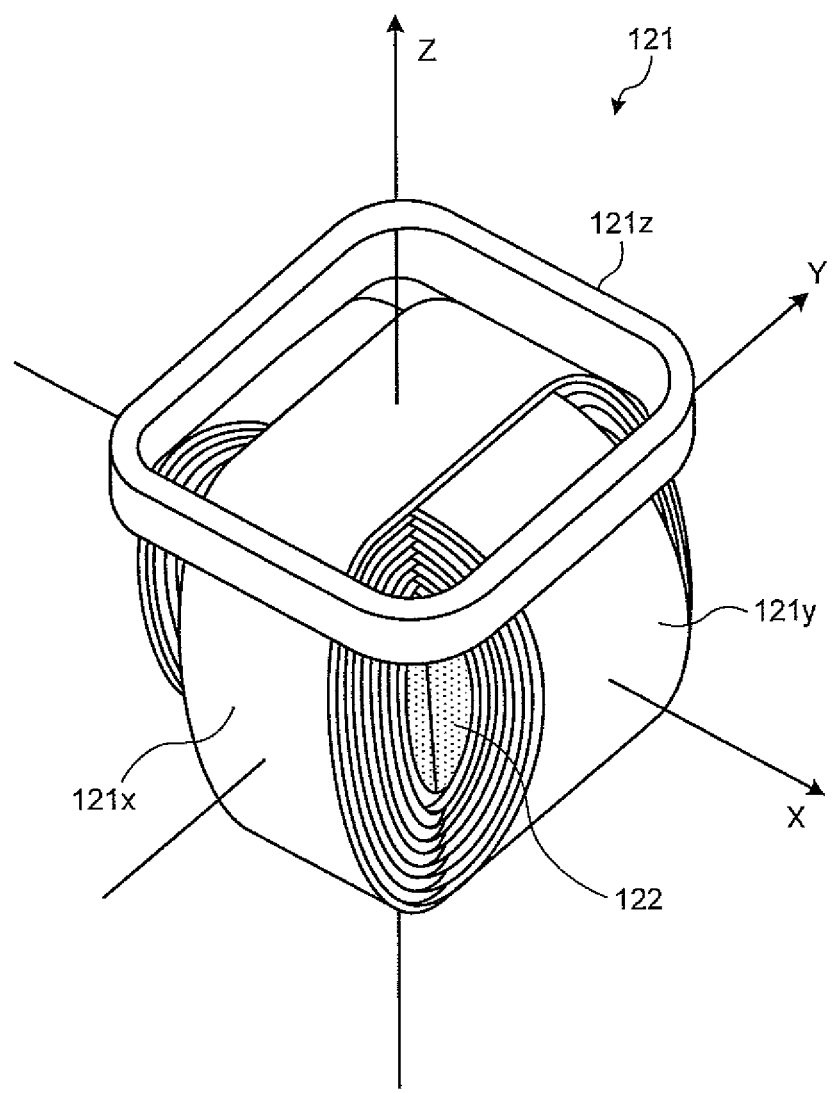
FIG. 20 is a view of an example of the magnetic field generator of the capsule medical device guidance system according to the present invention.

The magnetic field generator 2*a* generates a guiding magnetic field by a magnetic field generator realized by three-axis directional coils which, by being formed three-dimensionally in combination, generate respective magnetic fields in respective axis directions of the absolute coordinate system, for example. FIG. 20 is a view of an example of the magnetic field generator shown in FIG. 19. As shown in FIG. 20, the magnetic field generator according to the present invention is realized, for example like a magnetic field generator 121, by three-dimensionally combining an X axis coil 121*x* which generates a magnetic field in the X axis direction of the absolute coordinate system, a Y axis coil 121*y* which generates a magnetic field in the Y axis direction of the absolute coordinate system, and a Z axis coil 121*z* which generates a magnetic field in the Z axis direction of the absolute coordinate system. The X axis coil 121*x* and the Y axis coil 121*y* circumvolute an iron core 122 in a manner of being at right angles to each other. The Z axis coil 121*z* is arranged at an upper part of the X axis coil 121*x* and the Y axis coil 121*y*.

Figure 21A:
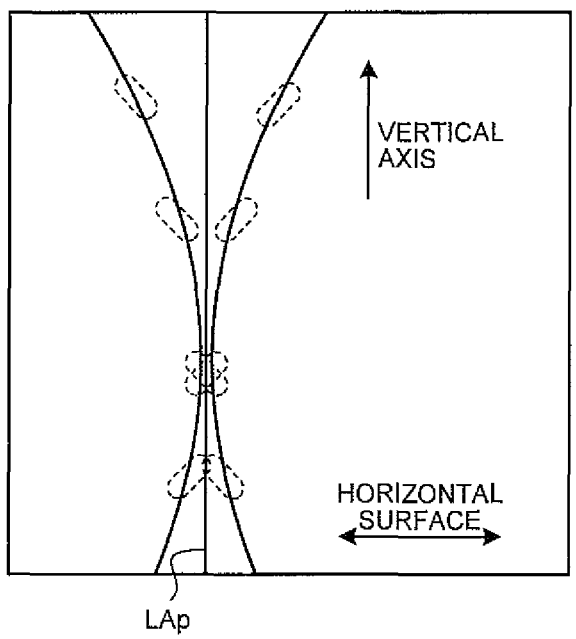
FIGS. 21A and 21B are explanatory views of a peak magnetic field to be generated by the magnetic field generator shown in FIG. 20.
Figure 21B:
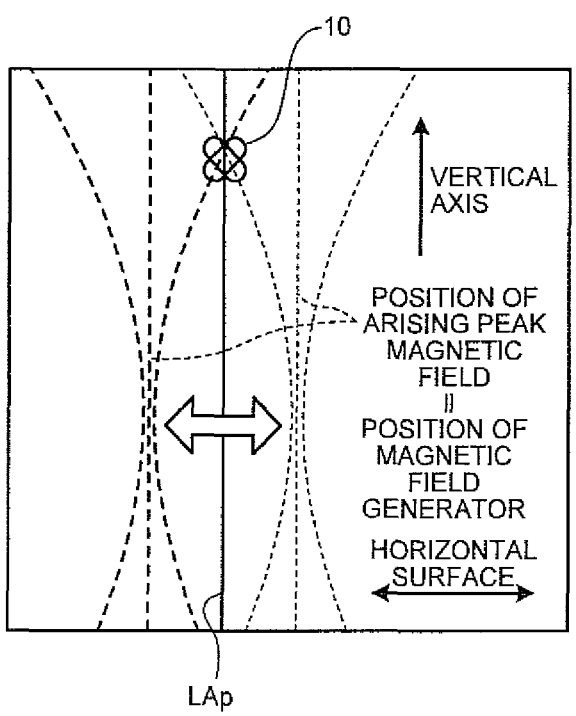

At the calibration process (at step S20 in FIG. 7 or at step S220 in FIG. 17), the magnetic field control instructing unit 45 changes, based on an amount of deviation of the peak position from the vertical axis LAp in the horizontal direction with respect to the attitude of the capsule endoscope 10 in the rotating direction at the detected vertical position of the capsule endoscope 10, the relative position between the magnetic field generator 2*a* that generates a peak magnetic field on the central axis and the bed 304 that supports the subject toward a direction of correcting the deviation of the peak position from the vertical axis LAp in the horizontal direction, the deviation being caused when the attitude of the capsule endoscope 10 in the rotating direction is changed depending on the attitude of the capsule endoscope 10 in the rotating direction. By changing the relative position between the magnetic field generator 2*a* that generates a peak magnetic field on the central axis and the bed 304 that supports the subject depending on the attitude of the capsule endoscope 10 as shown in FIG. 21B even when the center of the peak magnetic field changes depending on the attitude of the capsule endoscope 10 in the rotating direction as shown in FIG. 21A, it is possible to guide the capsule endoscope 10 while keeping the position of the capsule endoscope 10 in the vicinity of the vertical axis LAp. In the first and the second embodiments, a peak magnetic field inside the subject may be shifted and the peak magnetic field having a peak at a desired position inside the subject may be generated by controlling a power current supplied by the magnetic field controller 8 to the magnetic field generator 2.

While the case of the capsule endoscope 10 provided with a plurality of imaging units is taken as an example and explained in the first and the second embodiments, a monocular capsule endoscope provided with the imaging unit 11A only may be used.

While the case of the capsule endoscope 10 using the permanent magnet 19 is taken as an example and explained in the first and the second embodiments, the present invention is not limited thereto of course and a capsule endoscope provided with an electromagnet in place of the permanent magnet 19 may be used.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule medical device guidance system, comprising:
a capsule medical device that includes a magnetic-field responding unit;
a magnetic field generator that generates at least a gradient magnetic field in a vertical direction for the magnetic-field responding unit to guide the capsule medical device, the magnetic field generator being capable of changing a gradient distribution of the gradient magnetic field to be generated in the vertical direction;
an operation input unit through which operating information for magnetically guiding the capsule medical device is input;
a control unit that controls the magnetic field generator according to the operating information input through the operation input unit to guide the capsule medical device, the control unit controlling the magnetic field generator to change a gradient distribution of the gradient magnetic field to be generated in the vertical direction; and
a position detector that detects a position of the capsule medical device in the vertical direction based on a gradient distribution of the gradient magnetic field generated by the magnetic field generator, a physical parameter of the capsule medical device, and a physical parameter of a liquid when the capsule medical device starts to move, wherein
the control unit sets a magnetic field to be generated by the magnetic field generator based on the position of the capsule magnetic device in the vertical direction detected by the position detector;
the control unit controls the magnetic field generator to generate a gradient magnetic field having a gradient in a direction opposite to a direction of a resultant force of buoyancy of the capsule medical device and gravity of the capsule medical device, and controls, after controlling the magnetic field generator to generate a gradient magnetic field for bringing the capsule medical device in contact with a reference surface in an initial state, the magnetic field generator to gradually change the gradient distribution of the gradient magnetic field to be generated such that the capsule medical device is away from a reference surface, the reference surface being at least one of an upper boundary surface and a lower boundary surface of the liquid, and
the position detector detects the position of the capsule medical device in the vertical direction based on the gradient distribution of the gradient magnetic field generated by the magnetic field generator when the capsule medical device starts to move, the gradient distribution of the gradient magnetic field having been gradually changed.

2. The capsule medical device guidance system according to claim 1, wherein
a tilt of the capsule medical device that allows the capsule medical device to operate is predetermined based on the physical parameter of the capsule medical device and the physical parameter of the liquid, and
the position detector detects the position of the capsule medical device in the vertical direction depending on a position at which the tilt of the capsule medical device is in the vertical direction of the gradient magnetic field generated by the magnetic field generator when the capsule medical device starts to move.

3. The capsule medical device guidance system according to claim 2, wherein
the physical parameter of the capsule medical device includes a mass, a volume, and a magnetic moment of the capsule medical device, and
the physical parameter of the liquid includes a density of the liquid.

4. The capsule medical device guidance system according to claim 1, further comprising an operation start information input unit through which operation start information indicating that the capsule medical device starts to move is input, wherein
the position detector detects the position of the capsule medical device in the vertical direction based on the gradient distribution of the gradient magnetic field generated by the magnetic field generator when the operation start information is input through the operation start information input unit.

5. The capsule medical device guidance system according to claim 1, further comprising an operation detector that detects an operation of the capsule medical device, wherein
the position detector determines based on a detection result obtained by the operation detector whether the capsule medical device starts to move, the position detector detecting, when determining that the capsule medical device starts to move, the position of the capsule medical device in the vertical direction based on the gradient distribution of the gradient magnetic field generated by the magnetic field generator.

6. The capsule medical device guidance system according to claim 5, wherein
the capsule medical device includes
an imaging unit that captures an image inside a subject; and
a transmitting unit that transmits the image captured by the imaging unit to the outside, and
the operation detector detects the operation of the capsule medical device based on the image inside the subject transmitted from the capsule medical device.

7. The capsule medical device guidance system according to claim 1, wherein
the control unit controls the magnetic field generator to generate a most suitable magnetic field for guiding the capsule medical device in a region which is at a side opposite to the reference surface at the position of the capsule medical device in the vertical direction detected by the position detector.

8. A method for guiding a capsule medical device, comprising:
changing, by a control unit, a gradient distribution of a gradient magnetic field generated by a magnetic field generator in a vertical direction, the magnetic field generator generating at least the gradient magnetic field in the vertical direction to guide a capsule medical device that includes a magnetic-field responding unit;
detecting, by a position detector, a position of the capsule medical device in the vertical direction based on a gradient distribution of the gradient magnetic field generated by the magnetic field generator, a physical parameter of the capsule medical device, and a physical parameter of a liquid when the capsule medical device starts to move; and setting, by the control unit, the magnetic field generated by the magnetic field generator based on the detected position of the capsule medical device in the vertical direction;

wherein the changing includes controlling the magnetic field generator to generate a gradient magnetic field having a gradient in a direction opposite to a direction of a resultant force of buoyancy of the capsule medical device and gravity of the capsule medical device; and gradually changing, by the control unit, after controlling the magnetic field generator to generate a gradient magnetic field for bringing the capsule medical device in contact with a reference surface in an initial state, the gradient distribution of the gradient magnetic field to be generated such that the capsule medical device is away from a reference surface, the reference surface being at least one of an upper boundary surface and a lower boundary surface of the liquid, and the detecting includes detecting, by the position detector, the position of the capsule medical device in the vertical direction based on the gradient distribution of the gradient magnetic field generated by the magnetic field generator when the capsule medical device starts to move, the gradient distribution of the gradient magnetic field having been gradually changed at the changing.

9. The method for guiding a capsule medical device according to claim 8, wherein a tilt of the capsule medical device that allows the capsule medical device to operate is predetermined based on the physical parameter of the capsule medical device and the physical parameter of the liquid, and the detecting includes detecting, by the position detector, the position of the capsule medical device in the vertical direction depending on a position at which the tilt of the capsule medical device is in the vertical direction of the gradient magnetic field generated by the magnetic field generator when the capsule medical device starts to move.

10. The method for guiding a capsule medical device according to claim 9, wherein the physical parameter of the capsule medical device includes a mass, a volume, and a magnetic moment of the capsule medical device, and the physical parameter of the liquid includes a density of the liquid.

11. The method for guiding a capsule medical device according to claim 8, wherein operation start information indicating that the capsule medical device starts to move is input to the capsule medical device by an operation start information input unit, wherein the detecting includes detecting, by the position detector, the position of the capsule medical device in the vertical direction based on the gradient distribution of the gradient magnetic field generated by the magnetic field generator when the operation start information is input.

12. The method for guiding a capsule medical device according to claim 8, further comprising detecting, by an operation detector, an operation of the capsule medical device, wherein the detecting the position includes determining, by the position detector, based on a detection result obtained at the detecting the operation whether the capsule medical device starts to move; and detecting, by the position detector, when it is determined that the capsule medical device starts to move, the position of the capsule medical device in the vertical direction based on the gradient distribution of the gradient magnetic field generated by the magnetic field generator, the physical parameter of the capsule medical device, and the physical parameter of the liquid.

13. The method for guiding a capsule medical device according to claim 12, wherein the capsule medical device includes an imaging unit that captures an image inside a subject; and a transmitting unit that transmits the image captured by the imaging unit to the outside, and the detecting the operation includes detecting the operation of the capsule medical device based on the image inside the subject transmitted from the capsule medical device.

14. The method for guiding a capsule medical device according to claim 8, wherein the setting includes setting, by the control unit, a most suitable magnetic field for guiding the capsule medical device generated by the magnetic generator in a region which is at a side opposite to the reference surface at the position of the capsule medical device in the vertical direction detected at the detecting.

* * * * *